(12) United States Patent
Herget et al.

(10) Patent No.: US 7,341,717 B2
(45) Date of Patent: Mar. 11, 2008

(54) THERAPEUTIC TARGETS FOR TREATMENT OF HCV INFECTIONS, METHODS OF TREATING HCV INFECTIONS AND COMPOUNDS USEFUL THEREFOR

(75) Inventors: Thomas Herget, Planegg (DE); Matthew Cotten, München (DE); Sabine Obert, München (DE); Bert Klebl, München (DE)

(73) Assignee: GPC Biotech AG, Munich (DE)

( * ) Notice: Subject to any disclaimer, the term of this patent is extended or adjusted under 35 U.S.C. 154(b) by 301 days.

(21) Appl. No.: 10/723,719

(22) Filed: Nov. 26, 2003

(65) Prior Publication Data

US 2004/0152073 A1 Aug. 5, 2004

Related U.S. Application Data

(63) Continuation-in-part of application No. 10/342,054, filed on Jan. 14, 2003, now abandoned, which is a continuation-in-part of application No. PCT/EP02/04167, filed on Apr. 15, 2002.

(60) Provisional application No. 60/430,367, filed on Dec. 3, 2002, provisional application No. 60/283,345, filed on Apr. 13, 2001.

(30) Foreign Application Priority Data

Nov. 29, 2002 (DE) ............... 102 55 861

(51) Int. Cl.
*A61K 48/00* (2006.01)
*C12Q 1/70* (2006.01)
(52) U.S. Cl. ..................... 424/93.1; 514/400
(58) Field of Classification Search ............... 424/93.2, 424/228.1
See application file for complete search history.

(56) References Cited

U.S. PATENT DOCUMENTS

| 6,033,860 | A | 3/2000 | Lockhart et al. | |
|---|---|---|---|---|
| 6,040,140 | A | 3/2000 | Croce et al. | |
| 6,172,046 | B1 * | 1/2001 | Albrecht | 514/43 |
| 6,242,473 | B1 * | 6/2001 | Hellstrand et al. | 514/400 |
| 6,274,747 | B1 | 8/2001 | Strelchenok | |
| 6,326,397 | B1 | 12/2001 | Bollag et al. | |
| 6,403,554 | B2 | 6/2002 | Strelchenok | |

FOREIGN PATENT DOCUMENTS

| WO | WO 99/67362 A1 | 12/1999 |
|---|---|---|
| WO | WO 99/67362 A1 * | 12/1999 |

OTHER PUBLICATIONS

Hsu et al. Clinics in Liver disease 1999, vol. 3, pp. 901-915.*
Naka et al. J. Gene Virol. 2005, vol. 86, pp. 2787-2792.*
Sumpter et al. J. Virol. 2004, vol. 78, No. 21, pp. 11591-11604.*
Vuillermoz et al. J. Med. Virol. 2004, vol. 74, pp. 41-53.*
Look et al. Antiviral Research 1999, vol. 43, pp. 113-122.*
Reddy et al. Hepatology Feb. 2001, pp. 433-438.*
Bartenschlager et al., *Journal of General Virology*, 81:1631-1648 (2000).
Brigelius-Flohé, *Free Radical Biology and Medicine*, 27:951-965 (1999).
Chartier et al., *Journal of Virology*, 70:4805-4810 (1996).
Chu et al., *Journal of Nutrition*, 129:1846-1854 (1999).
Cohen, *Science*, 285:26-30 (1999).
Esworthy et al., *Biochimica et Biophysica Acta*, 1381:213-226 (1998).
Glotzer et al., *Journal of Virology*, 75:2421-2434 (2001).
Glotzer et al., *Nature*, 407:207-211 (2000).
Graham et al., *J. gen. Virol.*, 36:59-74 (1977).
Guha et al., *Lab Animal*, 34:39-47 (2005).
Heathcote et al., *New England Journal of Medicine*, 343:1673-1680 (2000).
Herget et al., *Journal of Neurochemistry*, 70:47-58 (1998).
Holben et al., *Journal of the American Dietetic Association*, 99:836-843 (1999).
Hoofnagle et al., *New England Journal of Medicine*, 336:347-356 (1997).
Houghton, Michael, *Fields Virology Third Edition*, Fields et al., eds (Lippencott-Raven Pub., Philadelphia), Chapter 32, pp. 1035-1058 (1996).
Houglum et al., *Gastroenterology*, 113:1069-1073 (1997).

(Continued)

*Primary Examiner*—Bruce R. Campell
*Assistant Examiner*—Bao Qun Li
(74) *Attorney, Agent, or Firm*—Yankwich & Associates, P.C.; Leon R. Yankwich; Michael R. Wesolowski

(57) ABSTRACT

The present invention relates to the human cellular protein glutathione peroxidase-gastrointestinal as a target for medical intervention against Hepatitis C virus (HCV) infections. Furthermore, the present invention relates to a method for the detection of compounds useful for prophylaxis and/or treatment of Hepatitis C virus infections and a method for detecting Hepatitis C virus infections in an individual or in cells. Also compositions, compounds, nucleic acid molecules (such as aptamers), mono- or polyclonal antibodies are disclosed which are effective for the treatment of HCV infections, and methods for prophylaxis and/or treatment of Hepatitis C virus infections or for the regulation of Hepatitis C virus production are disclosed.

10 Claims, 6 Drawing Sheets

OTHER PUBLICATIONS

Lemay et al., *Virology,* 101:131-143 (1980).
Lohmann et al., *Science,* 285:110-113 (1999).
Look et al., *Antiviral Research,* 43: 113-122 (1999).
Michou et al., *Journal of Virology,* 73:1399-1410 (1999).
Neri et al., *Panminerva Medica,* 42:187-192 (2000).
Rosen et al., *Molecular Medicine Today,* 5:393-399 (1999).
Russell, *Journal of General Virology,* 81:2573-2604 (2000).
Schiedermaier et al., *Hepatology* 32:4, Pt 2 of 2. Abstract 1437 (2000).
Schinazi et al., *Antiviral Chemistry & Chemotherapy,* 10:99-114 (1999).
Taylor et al., *Archives of Biochemistry and Biophysics,* 305:600-605 (1993).
Wingler et al., *European Journal of Biochemistry,* 259:149-157 (1999).
Wong et al., *American Journal of Public Health,* 90:1562-1569 (2000).
Zeuzem et al., *New England Journal of Medicine,* 343:1666-1672 (2000).
Zhang et al., *Medizinische Klinik,* 94:2-6 (1999).

* cited by examiner

A

B

THERAPEUTIC TARGETS FOR TREATMENT OF HCV INFECTIONS, METHODS OF TREATING HCV INFECTIONS AND COMPOUNDS USEFUL THEREFOR

CROSS-REFERENCE TO RELATED APPLICATIONS

The present application is a continuation-in-part of U.S. application Ser. No. 10/342,054, filed Jan. 14, 2003 now abandoned, which is a continuation-in-part of international application PCT/EP02/04167, filed Apr. 15, 2002 and designating the U.S., which claims priority to U.S. provisional application No. 60/283,345, filed Apr. 13, 2001. The present application also claims priority to German patent application No. DE 102 55 861.2, filed Nov. 29, 2002 and to U.S. provisional application Ser. No. 60/430,367, filed Dec. 3, 2002.

FIELD OF THE INVENTION

The present invention relates to the human cellular protein glutathione peroxidase-gastrointestinal (or gastrointestinal glutathione peroxidase, abbreviated GI-GPx) as a potential target for medical intervention against Hepatitis C virus (HCV) infections. Furthermore, the present invention relates to a method for the detection of compounds useful for prophylaxis and/or treatment of Hepatitis C virus infections and a method for detecting Hepatitis C virus infections in an individual or in cells. Also mono- or polyclonal antibodies are disclosed that are effective for the treatment of HCV infections together with methods for treating Hepatitis C virus infections or for the regulation of Hepatitis C virus production wherein genes or said antibodies may be used.

The present invention also relates to chemical compounds and substances which are effective against Hepatitis C virus (HCV) infections. In particular, compositions comprising said compounds and/or substances, use of the compounds and/or substances for the preparation of compositions useful for the prophylaxis and/or treatment of HCV infections, as well as methods for preventing and/or treating HCV infections.

BACKGROUND OF THE INVENTION

Hepatitis C Virus (HCV) infection is a major cause of chronic hepatitis, cirrhosis and hepatocellular carcinoma. The World Health Organization estimates that approximately 3% of the world population, or 170 million people, have been infected with the Hepatitis C virus. In the United States, an estimated 3.9 million Americans have been infected with HCV (CDC fact sheet September 2000). Over 80% of HCV-infected individuals develop chronic hepatitis, which is associated with disease states ranging from asymptomatic carrier states to repeated inflammation of the liver and serious chronic liver disease. Over the course of 20 years, more than 20% of chronic HCV-patients are expected to be at risk to develop cirrhosis or progress to hepatocellular carcinoma. Liver failure from chronic hepatitis C is the leading indicator for liver transplantation. Excluding transplantation, the CDC estimates that medical and work-loss cost for HCV annually are around $600 million.

HCV is transmitted primarily by blood and blood products. Due to routine screening of the blood supplies from mid-1992, new transfusion-related cases are exceedingly rare and have been surpassed by injection drug use as the highest risk factor for acquiring the virus. There is also a sexual, however inefficient, route of transmission, and a 6% rate of transmission from infected mothers to their children, which is higher in case of HIV co-infection. In a certain percentage of infections, the mode of transmission remains unknown. In spite of the significant decline in incidence in the 1990's, the number of deaths (estimated deaths annually at the moment: 8000 to 10,000 in U.S.) and of severe disease due to HCV is anticipated to triple in the next 10 to 20 years. (Sources: CDC fact sheets, accessed Dec. 12, 2000; Houghton, "Hepatitis C Viruses", in *Fields Virology*, B. N. Fields, D. M. Knipe, P. M. Howley, eds. (Lippencott-Raven Pub., Philadelphia, (1996); Rosen and Gretch, *Molecular Medicine Today*, 5: 393 (September 1999); *Science*, 285: 26 (July 1999): News Focus: The scientific challenge of Hepatitis C; Wong et al., *Am J Public Health*, 90: 1562 (October 2000), estimating future hepatitis C morbidity, mortality, and costs in the United States.)

According to the announcement from the EASL (European Association for the Study of the Liver) International Consensus Conference on Hepatitis C (Feb. 26-28, 1999, Paris, France), combination therapy of alpha interferon and ribavirin is the recommended treatment for naive patients. Monotherapy with interferon has also been approved by the FDA, but the sustained response rate (i.e., HCV RNA remains undetectable in the serum for more than 6 months after end of therapy) is only 15 to 20%, in contrast to 35 to 45% with combination therapy. Interferons (Intron A, Schering-Plough; Roferon A, Hoffmann-LaRoche; Wellferon, Glaxo Wellcome; Infergen, Amgen) are injected subcutaneously three times a week, ribavirin (Rebetol, Schering-Plough) is an oral drug given twice a day. Recommended treatment duration is 6 to 12 months, depending on HCV genotype. Experimental forms of slow-release pegylated interferons (Pegasys, Hoffmann-LaRoche; PEG-Intron, Schering-Plough) have shown improvements in response rates (42 to 82% in combination with ribavirin) and application (once-weekly injection) in recent clinical studies (Hepatology 32:4, Pt 2 of 2. October 2000; NEJM 343, 1673. December 2000; NEJM 343, 1666. December 2000). Common side effects of interferon therapy include: e.g., fatigue, muscle aches, head aches, nausea, fever, weight loss, irritability, depression, bone marrow suppression, reversible hair loss. The most common side effects of ribavirin are anemia, fatigue and irritability, itching, skin rash, nasal stuffiness, sinusitis, cough. More serious side effects of mono-and combination therapy occur in less than two percent of patients (NIDDK information: Chronic Hepatitis C: Current Disease Management; accessed Sep. 12, 1999). Some of the contraindications to interferon are psychosis or severe depression; neutropenia and/or thrombocytopenia; organ transplantation except liver; symptomatic heart disease; decompensated cirrhosis; uncontrolled seizures. Contraindications to ribavirin are end-stage renal failure; anemia; hemoglobinopathies; severe heart disease; pregnancy; no reliable method of contraception (consensus statement EASL). Moreover, treatment of Hepatitis C virus infection with interferon-alpha is effective in only a minority of individuals. This suggests that the virus may be resistant to interferon.

Moreover, although the combination therapy of interferon and ribavirin induces a sustained virologic response in up to 50 to 60% of cases, a significant number of patients do not respond to the combination therapy. (See, Hoofnagle J H, di Bisceglie A M, *N. Engl. J Med.* 1 336(5): 347-356 (1997)).

Other experimental treatments include: the administration of Maxamine (histamine dihydrochloride, Maxim Pharmaceuticals), which will be combined with Interferon in phase III studies; VX-497 (Vertex Pharmaceuticals), an IMP dehydrogenase inhibitor, as a less toxic ribavirin substitute in phase II; and amantadine (Endo Labs), an approved influenza drug, as the third component in triple therapy (phase II). Inhibitors for HCV enzymes such as protease inhibitors, RNA polymerase inhibitors, helicase inhibitors as well as ribozymes and antisense RNAs are under preclinical development (Boehringer Ingelheim, Ribozyme Pharmaceuticals, Vertex Pharmaceuticals, Schering-Plough, Hoffmann-LaRoche, Immusol, Merck, etc.). No vaccine is available for prevention or therapeutic use, but several companies are trying to develop conventional or DNA vaccines or immunostimulatory agents (e.g., Chiron, Merck/Vical, Epimmune, NABI, Innogenetics).

In addition, antibodies against HCV virion have been developed and entered into clinical trials recently (Trimera Co., Israel).

In summary, the available treatment for chronic Hepatitis C is expensive, effective only in a certain percentage of patients, and commonly leads to adverse side effects.

What is needed, therefore, is an alternate and effective approach to inhibiting HCV replication and for treating HCV infections in patients, particularly in patients who fail to respond to current therapies involving interferon.

SUMMARY OF THE INVENTION

The present invention is based upon the surprising discovery that the human cellular protein gastrointestinal glutathione peroxidase (P18283) is specifically downregulated as a result of HCV replication in HCV infected host cells. The antiviral therapeutic and/or prophylactic research approach described herein focuses on discovering the cellular signal transduction pathways involved in viral infections. Identification of the signal transduction molecules that are key to viral infection provides for, among other things, novel diagnostic methods, for example, assays and compositions useful therefor, novel targets for antiviral therapeutics, a novel class of antiviral therapeutics, and new screening methods (e.g., assays), and materials to discover new antiviral agents.

In one aspect, the present invention is directed to a method for detecting compounds useful for the prophylaxis and/or treatment of Hepatitis C virus infections comprising the steps of contacting a test compound with human cellular protein gastronintestinal glutathione peroxidase and detecting gastrointestinal glutathione peroxidase activity.

In another aspect, the present invention is directed to a method for detecting Hepatitis C virus infections in an individual comprising:
  a) providing a sample from said individual; and
  b) detecting activity in the sample of gastrointestinal glutathione peroxidase.

In another aspect, the present invention is directed to a method for detecting Hepatitis C virus infections in cells, cell cultures, or cell lysates, comprising:
  a) providing the cells, cell cultures, or cell lysates; and
  b) detecting activity in said cells, cell cultures, or cell lysates of human cellular protein gastrointestinal glutathione peroxidase.

In another aspect, the present invention is directed to a method for preventing and/or treating Hepatitis C virus infection and/or diseases associated with HCV infection comprising the step of administering a pharmaceutically effective amount of an agent which inhibits at least partially the activity of GI-GPx or which inhibits at least partially the production of GI-GPx.

In another aspect, the present invention is directed to a method for regulating the production of Hepatitis C virus in an individual, cells, cell culture, or cell lysates comprising the step of administering a pharmaceutically effective amount of an agent wherein said agent inhibits at least partially the activity of human cellular protein gastrointestinal glutathione peroxidase or wherein said agent at least partially inhibits the production of human cellular protein gastrointestinal glutathione peroxidase.

Accordingly, as disclosed in the present application, agents with an inhibitory activity for gastrointestinal glutathione peroxidase include, but are not limited to, monoclonal or polyclonal antibodies that bind to GI-GPx.

In yet another aspect, the present invention is directed to methods for preventing and/or treating Hepatitis C virus infection and/or diseases associated with HCV infection in an individual comprising the step of administering a pharmaceutically effective amount of an agent which activates at least partially the activity of human cellular protein gastrointestinal glutathione peroxidase or which activates or stimulates at least partially the production of human cellular protein gastrointestinal glutathione peroxidase.

In another aspect, the present invention is directed to a method for regulating the production of Hepatitis C virus in an individual, cells, cell culture, or cell lysates, comprising the step of administering a pharmaceutically effective amount of an agent wherein said agent activates at least partially the activity of human cellular protein gastrointestinal glutathione peroxidase or wherein said agent at least partially activates or stimulates the production of the human cellular protein gastrointestinal glutathione peroxidase.

In still another aspect, the present invention is directed to a method for regulating the expression of the human cellular protein gastrointestinal glutathione peroxidase in an individual, cells, cell culture, or cell lysates, comprising the step of administering a pharmaceutically effective amount of an agent wherein said agent inhibits at least partially the transcription of DNA and/or the translation of RNA encoding the human cellular protein gastrointestinal glutathione peroxidase.

Accordingly, as disclosed in the present application, agents which inhibit the transcription of DNA and/or the translation of RNA include, but are not limited to, oligonucleotides that bind the DNA and/or RNA coding for GI-GPx. Such oligonucleotides may be aptamers or antisense nucleic acid molecules.

The present invention is also directed to a method for regulating the expression of the human cellular protein gastrointestinal glutathione peroxidase in an individual, cell, cell culture, or cell lysate, comprising the step of administering a pharmaceutically effective amount of an agent wherein said agent activates at least partially the transcription of DNA and/or the translation of RNA encoding human cellular protein gastrointestinal glutathione peroxidase.

In addition, the present invention is directed to a method for regulating the activity of the human cellular protein gastrointestinal glutathione peroxidase in an individual, cell, cell culture, or cell lysate, comprising the step of administering a pharmaceutically effective amount of an agent wherein said agent interacts with the human cellular protein gastrointestinal glutathione peroxidase.

In another aspect, the present invention is directed to a method for the selective killing of HCV infected cells in an individual, cells, cell culture, or cell lysate, comprising the step of administering a pharmaceutically effective amount of a radical initiator which is capable of generating artificial oxidative stress conditions within the cells.

In yet another aspect, the present invention is directed to a method for preventing and/or treating HCV infections in an individual by at least partially compensating for the down-regulation of GI-GPx comprising the step of administering a pharmaceutically effective amount of at least one antioxidant which is capable of supporting the function of GI-GPx present within the cells.

In still another aspect, the present invention is directed to a method for at least partially compensating for the down-regulation of GI-GPx in an individual, cells, cell culture, or cell lysates, comprising the step of administering a pharmaceutically effective amount of at least one antioxidant which is capable of supporting the function of GI-GPx present within the cells.

The present invention is also directed to a composition useful for the prophylaxis and/or treatment of Hepatitis C virus and/or diseases associated with HCV infection in an individual, said composition comprising at least one agent capable of inhibiting activity of human cellular protein gastrointestinal glutathione peroxidase or capable of decreasing the expression of human cellular protein gastrointestinal glutathione peroxidase.

The present invention is also directed to a composition useful for the regulation of GI-GPx activity in an individual, cells, cell culture, or cell lysates, said composition comprising at least one agent capable of inhibiting activity of human cellular protein gastrointestinal glutathione peroxidase or capable of decreasing the expression of human cellular protein gastrointestinal glutathione peroxidase.

In another aspect, the present invention is directed to a composition useful for the prophylaxis and/or treatment of Hepatitis C virus and/or diseases associated with HCV infection in an individual, said composition comprising at least one agent capable of increasing the activity of human cellular protein gastrointestinal glutathione peroxidase or capable of activating or stimulating the expression of human cellular protein gastrointestinal glutathione peroxidase.

The present invention is also directed to a composition useful for the regulation of GI-GPx activity in an individual, cells, cell culture, or cell lysates, said composition comprising at least one agent capable of increasing the activity of human cellular protein gastrointestinal glutathione peroxidase or capable of activating or stimulating the expression of human cellular protein gastrointestinal glutathione peroxidase.

Accordingly, as disclosed in the present application, specific chemical substances and compounds that can be used alone or in combination to upregulate and/or activate the human cellular protein gastrointestinal glutathione peroxidase include, but are not limited to, selenium, selenium salts, Vitamin $D_3$, and retinoids. Particularly preferred retinoids include all forms of retinoic acid, including, but not limited to, 9-cis retinoic acid, salts of 9-cis retinoic acid, $C_1$-$C_{10}$ alkyl esters of 9-cis retinoic acid, salts of $C_1$-$C_{10}$ alkyl esters of 9-cis retinoic acid, $C_1$-$C_{10}$ alkyl amides of 9-cis retinoic acid, salts of $C_1$-$C_{10}$ alkyl amides of 9-cis retinoic acid, 13-cis retinoic acid, salts of 13-cis retinoic acid, $C_1$-$C_{10}$ alkyl esters of 13-cis retinoic acid, salts of $C_1$-$C_{10}$ alkyl esters of 13-cis retinoic acid, $C_1$-$C_{10}$ alkyl amides of 13-cis retinoic acid, salts of $C_1$-$C_{10}$ alkyl amides of 13-cis retinoic acid, retinol, retinoic acid adlehyde, etretinate, N-(4-hydroxyphenyl) retinamide (4-HPR), 6-[3-(1-adamantyl)-4-hydroxyphenyl]-2-naphthalene carboxylic acid (CD437; AHPN), all-trans-retinoic acid, $C_1$-$C_{10}$ esters and amides of all-trans-retinoic acid, paraquat, 4-[E-2-(5,6,7,8-tetrahydro-5,5,8,8-tetramethyl-2-naphthalenyl)-1-propenyl]benzoic acid, 4-hydroxyphenylretinamide, and 4-[(5,6,7,8-tetrahydro-5,5,8,8-tetramethyl-2-naphthalenyl)carboxamido]benzoic acid. Additionally, alpha interferon and/or ribavirin may be included to maximize the antiviral effect.

Because retinoic acid and other retinoids are well known, persons skilled in the art will be aware of various other retinoids which may be useful in practicing the methods of the present invention. For example, additional retinoids suitable for use in the present invention are disclosed in U.S. Pat. Nos. 6,274,747; 6,326,397; and Pat. No. 6,403,554, incorporated herein by reference.

In order to develop new pharmaceutically active compounds, a potential target for medical intervention has to be identified. Thus, processes for finding pharmaceutically effective compounds include target identification. Target identification is basically the identification of a particular biological component, namely a protein and its association with particular disease states or regulatory systems. A protein identified in a search for a pharmaceutically active chemical compound (drug) that can affect a disease or its symptoms is called a "target". Said target is involved in the regulation or control of biological systems and its function can be interfered with by a drug.

It is an object of the present invention to provide novel targets for medical intervention, prophylaxis and/or treatment of Hepatitis C virus infections in mammals, including humans, cells, cell cultures, or cell lysates together with methods for detecting HCV infections in individuals, cells, cell cultures and cell lysates, and methods for detecting compounds useful for prophylaxis and/or treatment of HCV infections. It is another object of the present invention to provide compounds, compositions and methods which are effective in the prophylaxis and/or treatment of Hepatitis C virus infections, but which lack the negative side-effects described above. A further object of the invention is to provide alternative, effective therapeutic treatments for HCV-infected patients, particularly patients who fail to respond to current anti-HCV combinatorial therapies, for example, patients who fail to successfully respond to interferon and ribavirin treatment. The object of the present invention is accomplished according to the teachings herein and the methods defined in the following independent claims. Further advantageous features, aspects and details of the invention are evident from the description, the examples, and the dependent claims of the present application.

DEFINITIONS

The word "disease" is used herein to refer to an acquired condition or genetic condition. A disease can alter the normal biological system of the body, causing an over- or under-abundance of chemical compounds (chemical imbalance). The regulatory systems for these chemical compounds involve the use by the body of certain proteins to detect imbalances or cause the body to produce neutralizing compounds in an attempt to restore the chemical balance.

The word "body" is used herein to refer to any biological system, e.g., human, animal, cells, cell culture, or cell lysates.

The term "associated diseases" refers to, for instance, opportunistic infections, liver cirrhosis, liver cancer, hepatocellular carcinoma, or any other diseases that can come along with HCV infection.

As used herein, the term "inhibitor" refers to any compound capable of downregulating, decreasing, inactivating, suppressing or otherwise regulating the amount and/or activity of GI-GPx or its expression. Generally, GI-GPx inhibitors may be proteins, oligopeptides and polypeptides, nucleic acids such as RNAi's, genes, small chemical molecules, or other chemical moieties. Small chemical molecules are, for instance, organic compounds with molecular weight typically below 500 g/mol and preferably also with less than 10 heteroatoms.

As used herein, the term "activator" refers to any chemical compound capable of upregulating, activating, stimulating, or increasing the amount and/or activity of GI-GPx or its expression. Generally, said agents may be proteins, oligo- and polypeptides, nucleic acids, genes, small chemical molecules, or other chemical moieties. An example for an activator of glutathione peroxidase is, e.g., selenium and retinoic acid (see, Brigelius-Flohé, 1999, *Free Radicals in Biology and Medicine*, 27: 951-965; Chu et al., 1999, *Journal of Nutrition*, 129:1846-1854).

The term "agent" is used herein as a synonym for regulator, inhibitor, and/or activator. Thus, the term "agent" refers to any chemical or biological compound capable of downregulating or upregulating, decreasing or increasing, suppressing or stimulating, inactivating or activating, or otherwise regulating or effecting the amount and/or activity of GI-GPx and/or the expression of GI-GPx.

One special kind of said agents are aptamers which function as regulators of the activity of a wide range of cellular molecules such as GI-GPx. Aptamers are nucleic acid molecules selected in vitro to bind small molecules, peptides, or proteins with high affinity and specificity. Aptamers not only exhibit highly specific molecular recognition properties but are also able to modulate the function of their cognate targets in a highly specific manner by agonistic or antagonistic mechanisms. The most familiar examples of aptamers are DNA aptamers or RNA aptamers.

In addition to their role in transmitting genetic information from DNA to proteins, RNA molecules participate actively in many cell processes. Examples are found in translation (rRNA, tRNA, tmRNA), intracellular protein targeting (SRP), nuclear splicing of pre-mRNA (snRNPs), mRNA editing (gRNA), and X-chromosome inactivation (Xist RNA). Each of these RNA molecules acts as a functional product in its own right, without coding any protein. Because RNA molecules can fold into unique shapes with distinct structural features, some RNAs bind to specific proteins or small molecules (as in the ATP-binding aptamer), while others catalyze particular chemical reactions. Thus, RNA aptamers can be used to interact with GI-GPx and thereby modulate, regulate, activate, or inhibit the activity and biological function of said peroxidase.

As used herein, the term "regulating expression and/or activity" generally refers to any process that functions to control or modulate the quantity or activity (functionality) of a cellular component. Static regulation maintains expression and/or activity at some given level. Upregulation refers to a relative increase in expression and/or activity. Accordingly, downregulation refers to a relative decrease in expression and/or activity. Downregulation is synonymous with inhibition of a given cellular component's activity.

Graph A: Blots were hybridized with radioactively labeled oligonucleotides (Probe 1: open bar and Probe 2: filled bar) complementary to the mRNA coding for human gastrointestinal glutathione peroxidase (GI-GPx). Membrane was exposed to Kodak x-ray films for one day at −80° C. with intensifier screens. The films were scanned and the density of the mRNA coding for GI-GPx calculated. The value for the control cells (pcDNA3) was set as 100% and compared with the values of the three replicon cell lines (±SEM), as indicated.

Graph B: Blots were stripped and re-hybridized with two oligonucleotides (Probe 1: open bars and Probe 2: filled bars) recognizing the classic glutathione peroxidase (cGPx) mRNA. Membrane was exposed to Kodak x-ray films for two days at −80° C. with intensifier screens. The film was densitometrically scanned, the intensities of the cGP mRNA of the control cell line pcDNA3 (set as 100%) compared with the replicon cell lines, as indicated. The data shown are the results of three independent experiments.

Figure 2:
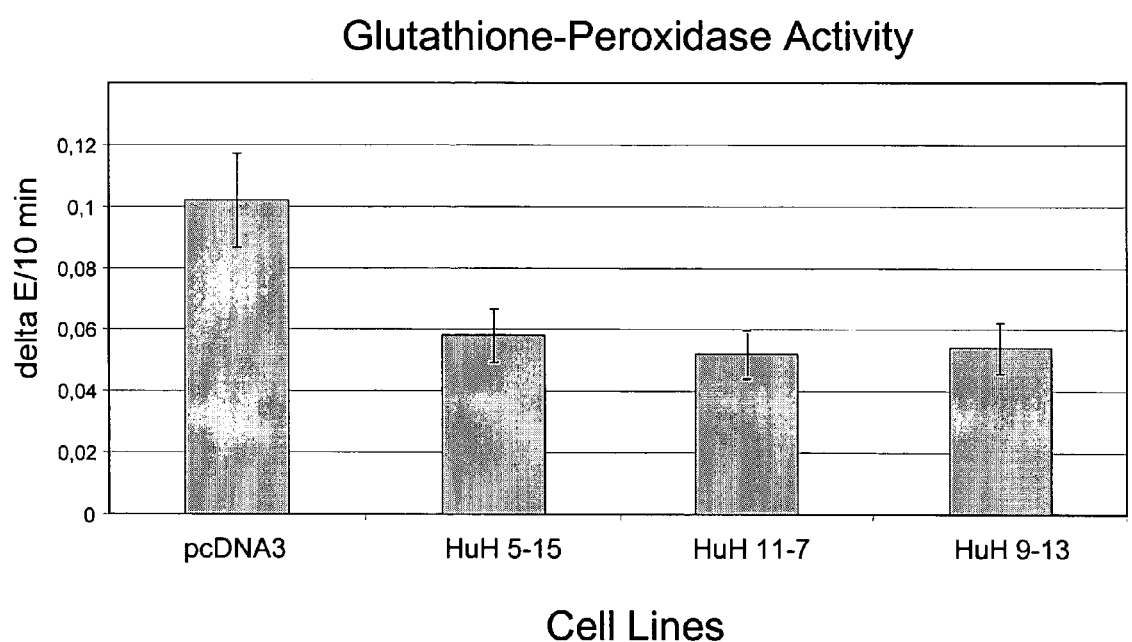

FIG. 2:
Cellular activity of glutathione peroxidase is reduced in replicon cell lines:
Cultures were plated and harvested as described in the examples section below. 180 µg protein of cytosolic extract were used for estimation of glutathione peroxidase activity as described infra. The mean change (±SEM) of extinction at 340 nm reflecting glutathione peroxidase activity for each cell line is illustrated.

Figure 3:
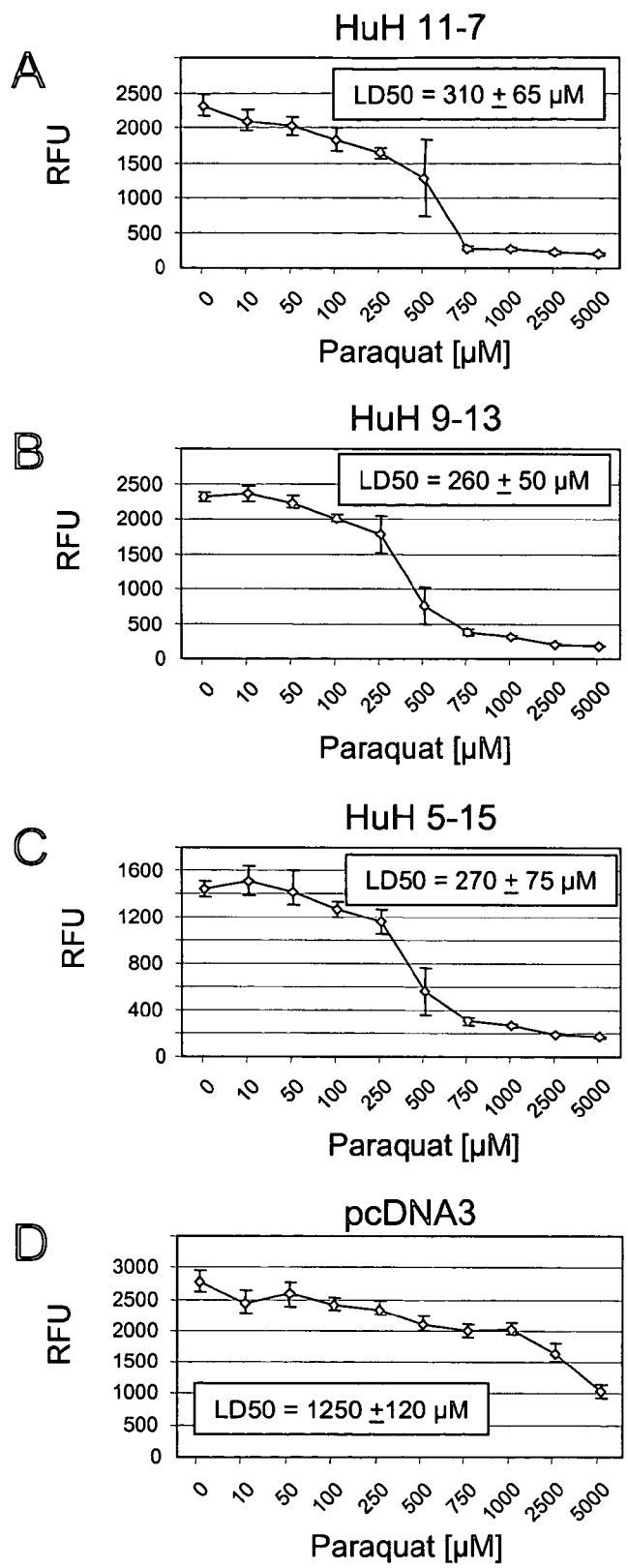

FIG. 3:
Replicon cells are susceptible towards oxidative stress:
Cells were plated in 96-well microtiter plates ($5 \times 10^3$ cells/0.35 cm$^2$) and after three days treated for 24 hours with the concentration of paraquat depicted. Cell viability was measured utilizing an Alamar-Blue assay and is reflected by relative fluorescence units (RFU) at 405 nm. The $LD_{50}$ values (±SEM) of three independent experiments are shown for each cell line.

Figure 4:
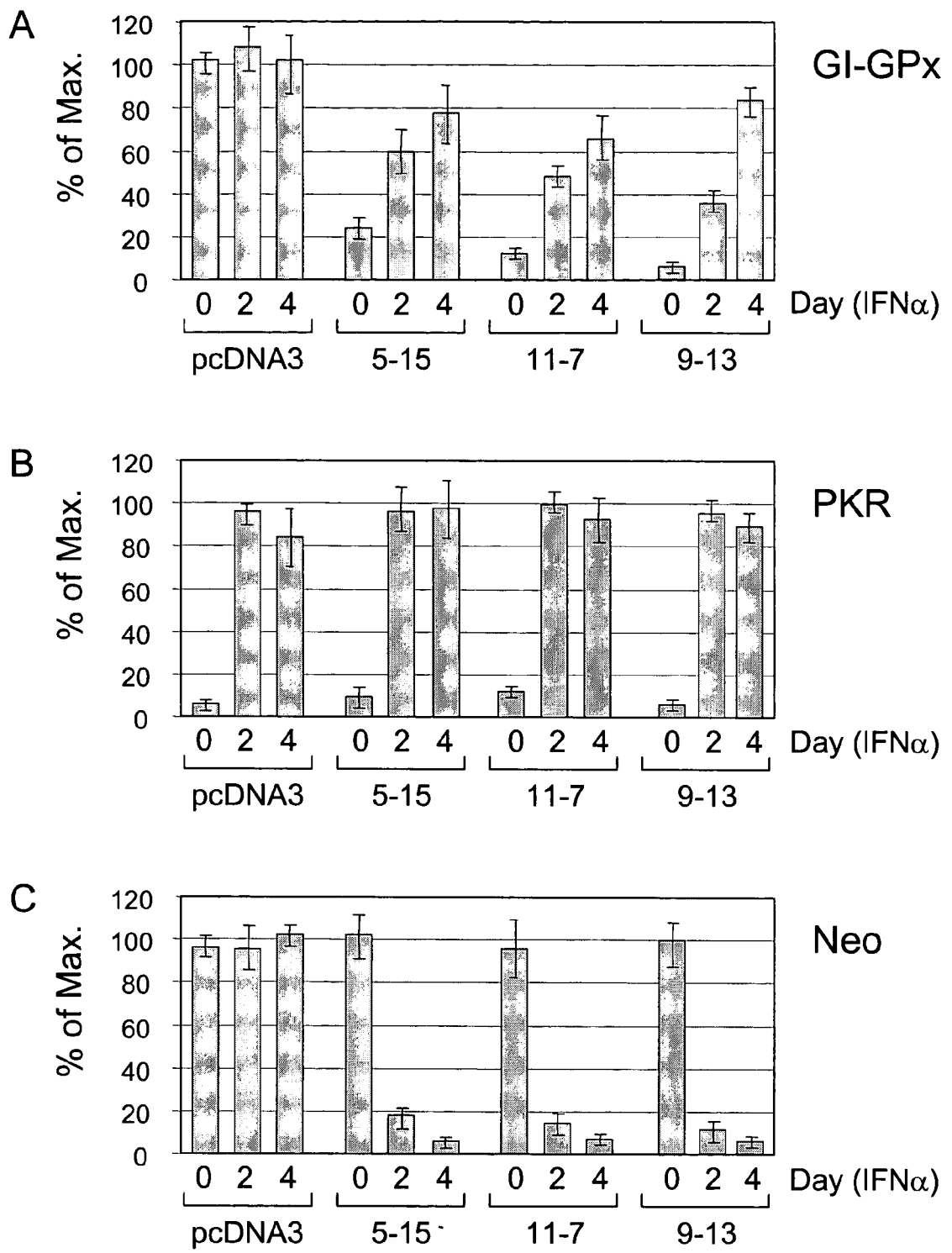

FIG. 4:
Effect of interferon on GI-GPx-, PKR- and genomic HCV-RNA levels:
The HuH7 pcDNA3 control cells and the replicon cell lines 5-15, 11-7 and 9-13 were plated as described in legend to FIG. 1 and after three days (Day 0) treated for two (Day 2) and four days (Day 4) with 1000U/ml interferon α (IFN-α). Then, cultures were harvested and RNA was prepared. 10 µg of total RNA were used for Northern blot analysis. For detection of GI-GPx (A) Probe 1 was used (see FIG. 1). The membranes were stripped and successively hybridized with probes for PKR (B) and neomycin phosphotransferase (Neo)(C).

Exposure time for all blots was two days at −80° C. with intensifier screen. The autoradiograms were densitometrically scanned and the values compared with the maximal value obtained with each probe in the respective experiment. The values depicted (±SEM) are obtained from three independent experiments.

Figure 5:
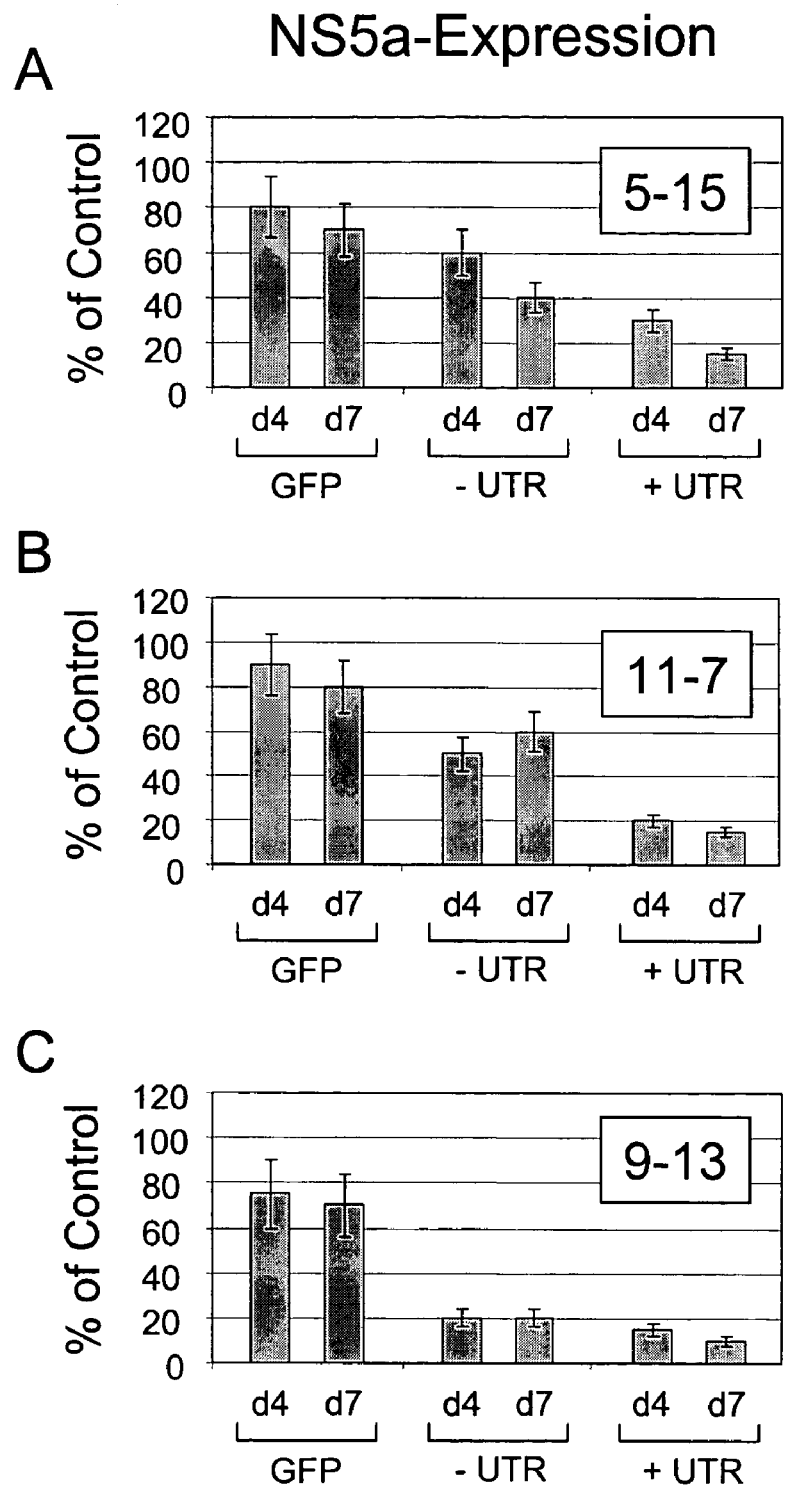
Figure 6:
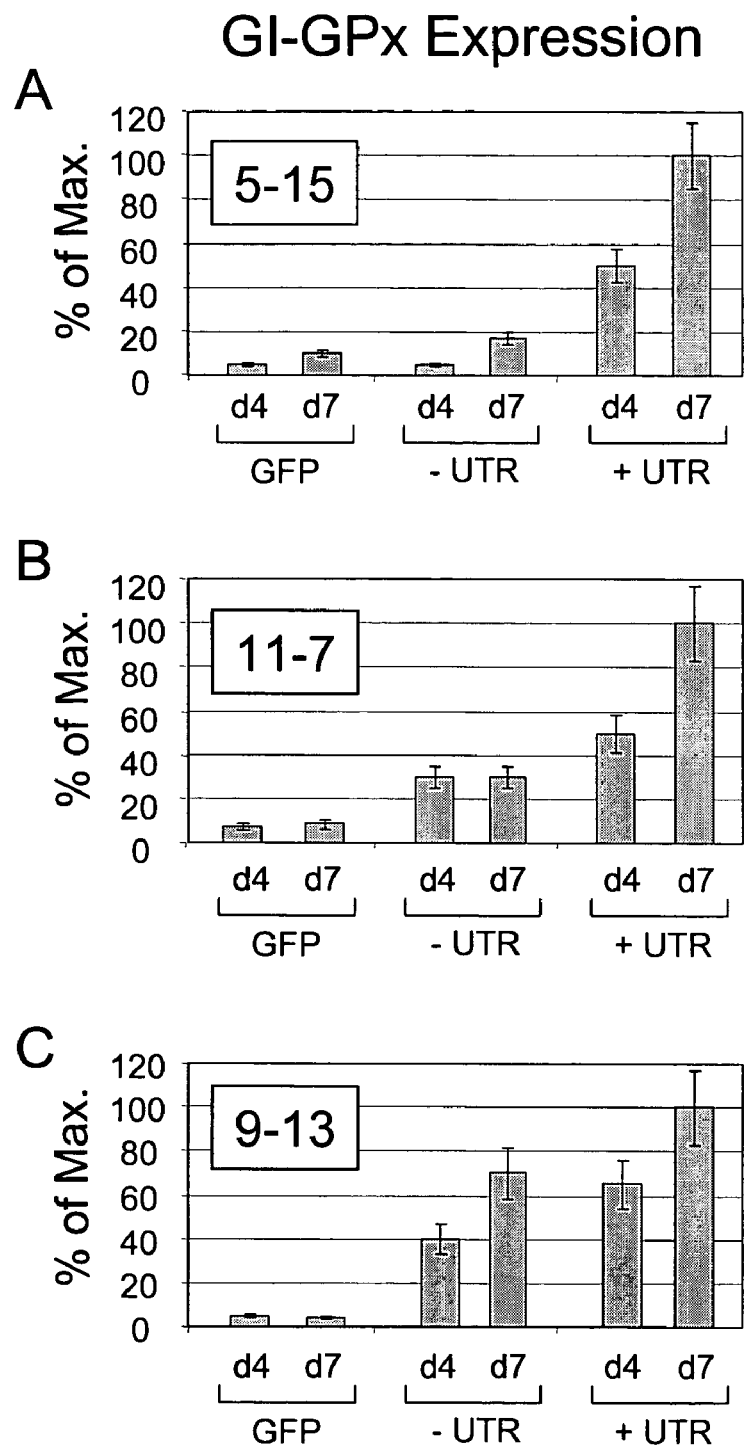

FIG. 5 and FIG. 6:
Overexpression of GI-GPx in replicon cells causes downregulation of HCV:
The replicon cell lines 5-15, 11-7 and 9-13 were plated at a density of $10^5$ cells per well of a 6-well plate and infected with $10^3$ Adenovirus particles/cell containing either the green fluorescent protein (GFP) as negative control, the GI-GPx cDNA without the 3'UTR (−UTR) and with the 3'UTR containing the SECIS (+UTR), as indicated.

After four (d4) and seven days (d7) post-infection, cultures were harvested and 10 μg protein separated on a 12.5% polyacrylamide gel. Western blot analysis was performed using an NS5a antibody (FIG. 5). Expression of the transduced GI-GPx cDNA was monitored with a GI-GPx-specific antiserum (FIG. 6).

The x-ray films were densitometrically scanned and the NS5a values compared with untransfected control cells (set as 100%) (FIG. 5) and the GI-GPx values compared with the maximum expression of the transduced GI-GPx cDNA obtained seven days post infection (set as 100%) (FIG. 6).

A considerable over-expression of the GI-GPx protein was observed, when cells were infected with the GI-GPx +3'UTR virus and slight over-expression of GI-GPx was observed with the GI-GPx −3'UTR virus (FIG. 6).

The data show a drastic down-regulation of the HCV protein NS5a in all replicon cell lines infected with the GI-GPx+3'UTR virus (FIG. 5).

Loading efficiency and integrity of proteins was controlled with a tubulin antibody (data not shown). The values depicted (±SEM) are obtained from three independent experiments.

DETAILED DESCRIPTION OF THE INVENTION

Recent research has revealed how cells communicate with each other to coordinate the growth and maintenance of the multitude of tissues within the human body. A key element of this communication network is the transmission of a signal from the exterior of a cell to its nucleus, which results in the activation or suppression of specific genes. This process is called signal transduction.

Signal transduction at the cellular level refers to the movement of signals from outside the cell to inside. The movement of signals can be simple, like that associated with receptor molecules of the acetylcholine class: receptors that constitute channels which, upon ligand interaction, allow signals to be passed in the form of small ion movement, either into or out of the cell. These ion movements result in changes in the electrical potential of the cells that, in turn, propagates the signal along the cell. More complex signal transduction involves the coupling of ligand-receptor interactions to many intracellular events. These events include phosphorylations by tyrosine kinases and/or serine/threonine kinases. Protein phosphorylations change enzyme activities and protein conformations. The eventual outcome is an alteration in cellular activity and changes in the program of genes expressed within the responding cells.

Signal transducting receptors are of three general classes:

1. Receptors that Penetrate the Plasma Membrane and Have Intrinsic Enzymatic Activity:

Receptors that have intrinsic enzymatic activities include those that are tyrosine kinases (e.g., PDGF, insulin, EGF and FGF receptors), tyrosine phosphatases (e.g., CD45 protein of T cells and macrophages), guanylate cyclases (e.g. natriuretic peptide receptors) and serine/threonine kinases (e.g. activin and TGF-beta receptors). Receptors with intrinsic tyrosine kinase activity are capable of autophosphorylation as well as phosphorylation of other substrates.

Additionally, several families of receptors lack intrinsic enzyme activity, yet are coupled to intracellular tyrosine kinases by direct protein-protein interactions. This class of receptors includes all of the cytokine receptors (e.g., the interleukin-2 receptor) as well as the CD4 and CD8 cell surface glycoproteins of T cells and the T cell antigen receptor.

2. Receptors that are Coupled, Inside the Cell, to GTP-Binding and Hydrolyzing Proteins (Termed G-Proteins):

Receptors of the class that interact with G-proteins all have a structure that is characterized by seven transmembrane-spanning domains. These receptors are termed serpentine receptors. Examples of this class are the adrenergic receptors, odorant receptors, and certain hormone receptors (e.g., glucagon, angiotensin, vasopressin, and bradykinin).

3. Receptors that are Found Intracellularly and that Upon Ligand Binding Migrate to the Nucleus where the Ligand-Receptor Complex Directly Affects Gene Transcription:

The steroid/thyroid hormone receptor superfamily (e.g., glucocorticoid, vitamin D, retinoic acid, and thyroid hormone receptors) is a class of proteins that reside in the cytoplasm and bind the lipophilic steroid/thyroid hormones. These hormones are capable of freely penetrating the hydrophobic plasma membrane. Upon binding ligand the hormone-receptor complex translocates to the nucleus and bind to specific DNA sequences resulting in altered transcription rates of the associated gene.

When the message reaches the nucleus via one or several of the pathways described above, it initiates the modulation of specific genes, resulting in the production of RNA and finally proteins that carry out a specific biological function. Disturbed activity of signal transduction molecules may lead to the malfunctioning of cells and disease processes.

The antiviral therapeutic and/or prophylactic research approach described herein focused on discovering the cellular signal transduction pathways involved in Hepatitis C viral infections. Identification of the signal transduction molecules that are key to HCV infection and persistence provides for, inter alia, novel targets for HCV antiviral therapeutics, novel classes of HCV antiviral therapeutics, and new screening methods (e.g., assays), and materials to discover new antiviral agents, and novel HCV diagnostic methods.

It is now revealed for the first time that the human cellular protein gastrointestinal glutathione peroxidase (GI-GPx) is specifically downregulated in a body as a result of HCV infection. This human cellular protein gastrointestinal glutathione peroxidase has been identified as a novel diagnostic and therapeutic target for HCV infection.

Glutathione Peroxidase:

Four distinct species of glutathione peroxidase have been identified in mammals to date, the classical cellular enzyme, the phospholipid hydroperoxide metabolizing enzyme, the gastroinestinal tract enzyme, and the extracellular plasma enzyme. Their primary structures are poorly related. It has been shown that they are encoded by different genes and have different enzymatic properties. The physiological role of the human plasma enzyme remains still unclear due to the low levels of reduced glutathione in human plasma and the low reactivity of this enzyme.

The human cellular protein glutathione peroxidase-gastrointestinal (GI-GPx) is also known as gastrointestinal glutathione peroxidase, glutathione peroxidase-related protein 2 (GPRP) or glutathione hydrogen peroxide oxidoreductase. It has been assigned to the Accession Number P18283 and the EC Number 1.11.1.9.

GI-GPx catalyzes the reduction of various organic hydroperoxides, as well as hydrogen peroxide, with glutathione (GSH) as hydrogen donor ($2GSH+H_2O_2 \rightarrow GS-GS+2H_2O$).

It has a molecular weight of 84,000 and 4 subunits per mol of enzyme. The enzyme is useful for enzymatic determination of lipid hydroperoxide.

GI-GPx belongs to the family of selenoproteins and plays an important role in the defense mechanisms of mammals, birds and fish against oxidative damage by catalyzing the reduction of a variety of hydroperoxides, using glutathione as the reducing substrate. It has been suggested that this enzyme functions as a mechanism of protecting the cellular membrane system against peroxidative damage and that selenium as an essential trace element, may play an important role in this suggested function of the enzyme. It is known that both vitamin E and selenium (Se) act as antioxidants also in a common mechanism of oxidative stress as an underlying cause of genetic changes.

Selenium functions within mammalian systems primarily in the form of selenoproteins. Selenoproteins contain selenium as selenocysteine and perform a variety of physiological roles. Seventeen selenoproteins have been identified: cellular or classical glutathione peroxidase; plasma (or extracellular) glutathione peroxidase; phospholipid hydroperoxide glutathione peroxidase; gastrointestinal glutathione peroxidase; selenoprotein P; types 1, 2, and 3 iodothyronine deiodinase; selenoprotein W; thioredoxin reductase; and selenophosphate synthetase. Of these, cellular and plasma glutathione peroxidase are the functional parameters used for the assessment of selenium status (Holben and Smith, 1999, *J. Am. Diet. Assoc.*, 99:836-843).

In addition to vitamin E (DL-α-tocopherol), vitamin C (L-ascorbic acid), co-enzyme Q10, zinc, and selenium, many other antioxidants such as N-acetyl-L-cycteine, N-acetyl-S-farnesyl-L-cysteine, Bilirubin, caffeic acid, CAPE, catechin, ceruloplasmin, Coelenterazine, copper diisopropylsalicylate, deferoxamine mesylate, R-(-)-deprenyl, DMNQ, DTPA dianhydride, Ebselen, ellagic acid, (-)-epigallocatechin, L-ergothioneine, EUK-8, Ferritin, glutathione, glutathione monoethylester, α-lipoic acid, Luteolin, Manoalide, MCI-186, MnTBAP, MnTMPyP, morin hydrate, NCO-700, NDGA, p-Nitroblue, propyl gallate, Resveratrol, rutin, silymarin, L-stepholidine, taxifolin, tetrandrine, tocopherol acetate, tocotrienol, Trolox®, U-74389G, U-83836E, and uric acid (all available from Calbiochem, San Diego, Calif., U.S.A.) can be applied within the disclosed methods for preventing and/or treating HCV infections by compensating at least partially for the down-regulation of GI-GPx.

Additional antioxidants may be selected from the group of carboxylic acids such as citric acid and phenolic compounds such as BHA (butylated hydroxyanisole), BHT (butylated hydroxytoluene), propyl gallate, TBHQ (tert-butyl hydroquinone), tocopherols, lecithin, gums and resin guiac, THBP (trihydroxybutyrophenone), thiodipropionic acid and dilauryl thiodipropionate, and glycines.

Oxidative damage is mainly caused by free radicals, particularly reactive oxygen intermediates, derived from normal cellular respiration and oxidative burst produced when phagocytic cells destroy bacteria or virus-infected cells. In order to cope with the constant generation of potentially damaging oxygen radicals, eukaryotic organisms have evolved many defense mechanisms. These include the above-mentioned antioxidants which act as free radical scavengers and which may interact with GI-GPx and/or may activate, stimulate, and/or increase the expression and/or production of GI-GPx. This advantageous effect of the antioxidants on the amount of GI-GPx generated in the cells competes with the HCV-induced down-regulation of GI-GPx and supports the cells in their fight against the Hepatitis C viruses.

HCV Infection Studies:

The only reliable experimental HCV infection studies have been performed with chimpanzees. So far, there is no simple cell culture infection system available for HCV. Although a number of reports have been published describing in vitro propagation attempts of HCV in primary cells and cell lines, questions remain concerning reproducibility, low levels of expression and properly controlled detection methods (reviewed in *J. Gen Virol.*, 81: 1631; *Antiviral Chemistry and Chemotherapy*, 10: 99). For this reason, has been extremely difficult to study how HCV infects cells and to test anti-viral drugs in a model system (the only animals that can be infected are humans and chimpanzees). A major step in devising a culture system for HCV was established by the replicon cell lines (see, Lohmann et al., Replication of subgenomic hepatitis C virus RNAs in a hepatoma cell line, *Science*, 285: 110-113 (1999)). Replication of subgenomic HCV RNAs in cultured hepatocytes were obtained for the first time. These subgenomic replicons are composed of only the part of the HCV genome that encodes the non-structural proteins but are competent to be replicated in cells and to synthesize viral proteins. The replicons described in the scientific article of Lohmann et al., supra, and used in making the discoveries disclosed herein allows studies of HCV replication, pathogenesis and evolution in cell culture. They may also allow for cell-based testing of certain types of anti-viral drugs.

Thus, the replicon system described by Lohmann et al., supra, reproduces a crucial part of the HCV replication cycle which is used as a system for simulating HCV infection. Lohmann et al. produced bicistronic recombinant RNAs, so-called "replicons", which carry the neomycin-phosphotransferase (NPT) gene as well as a version of the HCV genome where the sequences for the structural HCV proteins were deleted. After transfection of the subgenomic HCV RNA molecules into the human hepatoma cell line HuH7, cells supporting efficient RNA-dependent RNA replication of the HCV replicons were selected based on co-amplification of the NPT gene and resulting resistance to the antibiotic G-418. Integration of coding information into the cellular genome was an exclusion criteria for functional replicons. Several lines were established from G-418 resistant clones with autonomously replicating HCV RNAs detectable by Northern Blotting. Minus-strand RNA replication intermediates were detected by Northern Blotting or metabolic radio-labeling, and the production of nonstructural HCV proteins was demonstrated by immuno-precipitation after metabolic labeling or Western Blotting.

Possible influences and/or dependencies of HCV's RNA-dependent RNA replication and nonstructural proteins on host cell transcription are accessible to analysis with the Clontech cDNA arrays used in the inventive methods described herein. HuH-pcDNA3 cells are HuH7 cells resistant to G-418 by integration of a NPT gene-carrying plasmid (pcDNA3, Invitrogen) and serve as a negative control. Three replicon lines were analyzed for changes in cellular RNA expression patterns compared to the control line:

HuH-9-13: a cell line with persistant replicon I377/NS3-3'/wt, described by Lohmann et al., supra, HuH-5-15: a cell line with persistant replicon I389/NS3-3'/wt, described by Lohmann et al., supra, HuH-11-7: a cell line with persistant replicon I377/NS2-3'/wt, described by Lohmann et al., supra.

These HCV replicon cells serve as a system for simulation of HCV infected cell systems, especially for simulating HCV infected mammals, including humans. Interference of HCV with the cellular signaling events is reflected in differential gene expression when compared to cellular signaling in control cells. Results from this novel signal transduction microarray analysis revealed significant downregulation of GI-GPx. Radioactively-labeled complex cDNA probes from HCV Replicon cells HuH-9-13, HuH-5-15, and HuH-11-7 were hybridized to cDNA arrays and compared to hybridizations with cDNA probes from HuH-pcDNA control cells which did not contain HCV Replicons.

Based on the surprising results reported herein, one aspect of the present invention is directed to a screening method for detecting compounds useful for the prophylaxis and/or treatment of Hepatitis C virus infections. Specifically, this method involves contacting a test compound with GI-GPx and detecting the GI-GPx activity. Such methods are advantageously carried out using cell-based techniques, where GI-GPx activity (e.g., GI-GPx transcription) can be measured (e.g., by Northern blotting, see Example 14, infra). Test compounds that enhance the activity of GI-GPx are identified as compounds for treating HCV infections. Alternatively, inhibitors of GI-GPx activity may be identified in this manner and may be used to promote the selective killing of HCV infected cells, in which GI-GPx is already down-regulated.

Another aspect of the present invention is directed to specific chemical substances and compounds, which, alone or in combination, are useful for the prophylaxis and/or treatment of Hepatitis C virus infections. Specifically, these chemical substances and compounds comprise selenium, selenium salts, Vitamin $D_3$, and retinoids. Particularly preferred retinoids include all forms of retinoic acid, including, but not limited to, 9-9-cis retinoic acid, salts of 9-cis retinoic acid, $C_1$-$C_{10}$ alkyl esters of 9-cis retinoic acid, salts of $C_1$-$C_{10}$ alkyl esters of 9-cis retinoic acid, $C_1$-$C_{10}$ alkyl amides of 9-cis retinoic acid, salts of $C_1$-$C_{10}$ alkyl amides of 9-cis retinoic acid, 13-cis retinoic acid, salts of 13-cis retinoic acid, $C_1$-$C_{10}$ alkyl esters of 13-cis retinoic acid, salts of $C_1$-$C_{10}$ alkyl esters of 13-cis retinoic acid, $C_1$-$C_{10}$ alkyl amides of 13-cis retinoic acid, salts of $C_1$-$C_{10}$ alkyl amides of 13-cis retinoic acid, retinol, retinoic acid adlehyde, etretinate, N-(4-hydroxyphenyl) retinamide (4-HPR), 6-[3-(1-adamantyl)-4-hydroxyphenyl]-2-naphthalene carboxylic acid (CD437; AHPN), all-trans-retinoic acid, $C_1$-$C_{10}$ esters and amides of all-trans-retinoic acid, paraquat, 4-[E-2-(5,6,7,8-tetrahydro-5,5,8,8-tetramethyl-2-naphthalenyl)-1-propenyl]benzoic acid, 4-hydroxyphenylretinamide, and 4-[(5,6,7,8-tetrahydro-5,5,8,8-tetramethyl-2-naphthalenyl) carboxamido]benzoic acid.

An additional aspect of the present invention is directed to the use of a combination of compounds for the prophylaxis and/or treatment of Hepatitis C virus infection. Such combinations preferably include, but are not limited to, one or more selenium compounds, especially selenium and selenium salts, in combination with one or more retinoid compounds, especially retinoic acid, including all-trans-retinoic acid, 9-cis retinoic acid and/or 13-cis retinoic acid. Also contemplated are combination therapies which include alpha interferon and/or ribavirin in combination with selenium compounds and retinoids. Particularly preferred combination therapeutics include alpha interferon in combination with selenium or selenium salt(s) also in combination with retinoic acid (most preferably all-trans-retinoic acid, 9-cis retinoic acid and/or 13-cis retinoic acid).

Another aspect of the present invention is directed to a diagnostic method, for example, an assay for detecting Hepatitis C virus infections in an individual or in cells. This method involves providing a sample from the individual or providing cells and detecting activity of GI-GPx.

Suitable samples for such methods include, for instance, blood, biopsies, cells, cell cultures, or cell lysates of liver or of any other tissue infected with HCV.

Accordingly, one aspect of the present invention is directed to novel compounds useful in the above-identified methods. Therefore, the present invention relates to monoclonal or polyclonal antibodies that bind to GI-GPx.

In addition, the present invention discloses a method for treating Hepatitis C virus infection in an individual comprising the step of administering a pharmaceutically effective amount of an agent which inhibits at least partially the activity of GI-GPx or which inhibits at least partially the production of GI-GPx in the cells.

Furthermore, the present invention discloses a method for treating Hepatitis C virus infection in an individual comprising the step of administering a pharmaceutically effective amount of at least one of the specific chemical compounds and substances referred to above, which upregulates at least partially the activity of GI-GPx or which upregulates at least partially the production of GI-GPx in the cells.

A similar aspect of the present invention is directed to a method for preventing and/or treating Hepatitis C virus infection and/or diseases associated with HCV infection in an individual comprising the step of administering a pharmaceutically effective amount of an agent which inhibits at least partially the activity of GI-GPx or which inhibits at least partially the production of GI-GPx.

Another aspect of the present invention is directed to a method for preventing and/or treating Hepatitis C virus infection and/or diseases associated with HCV infection in an individual, comprising the step of administering a pharmaceutically effective amount of at least one of the specific chemical compounds and substances referred to above, which upregulates at least partially the activity of GI-GPx or which upregulates at least partially the production of GI-GPx.

Another object of the present invention is to provide a method for regulating the production of Hepatitis C virus in an individual or in cells, cell cultures, or cell lysates comprising the step of administering a pharmaceutically effective amount of an agent wherein said agent inhibits at least partially the activity of GI-GPx or wherein said agent at least partially inhibits the production GI-GPx in the cells. The above-mentioned monoclonal or polyclonal antibodies directed against GI-GPx may be used as pharmaceutically active agents within said methods.

Another aspect of the present invention is to provide a method for regulating the production of Hepatitis C virus in an individual or in cells, cell cultures, or cell lysates comprising the step of administering a pharmaceutically effective amount of at least one of the specific chemical compounds and substances referred to above, which at least partially upregulate the activity GI-GPx or which at least partially upregulate the production of GI-GPx in the cells.

In addition to the above-mentioned methods the present invention is also directed to a method for preventing and/or treating Hepatitis C virus infection and/or diseases associated with HCV infection in an individual comprising the step of administering a pharmaceutically effective amount of an agent which activates at least partially GI-GPx or which activates or stimulates the production of GI-GPx in the cells of the individual.

In addition to the above-mentioned methods the present invention is also directed to a method for preventing and/or treating Hepatitis C virus infection and/or diseases associated with HCV infection in an individual comprising the step of administering a pharmaceutically effective amount of at least one of the specific chemical compounds and substances referred to above, which activates at least partially GI-GPx or which activates or stimulates the production of GI-GPx in the individual.

Another inventive aspect of the present invention is related to a method for preventing and/or treating Hepatitis C virus infection and/or diseases associated with HCV infection in an individual comprising the step of administering a pharmaceutically effective amount of an agent which activates at least partially the activity of GI-GPx or which activates or stimulates at least partially the production of GI-GPx.

In addition, the present invention is related to a method for regulating the effects of Hepatitis C virus infection and/or diseases associated with HCV infection in cells, cell cultures, or cell lysates comprising the step of administering a pharmaceutically effective amount of at least one of the specific chemical compounds and substances referred to above, which activates at least partially the activity of GI-GPx or which activate or stimulate at least partially the production of GI-GPx.

The function of GI-GPx is to detoxify peroxides in cells and prevent the cells from oxidative damage. As demonstrated in FIG. 3, subjecting HCV infected cells to oxidative stress conditions, preferably induced by paraquat or radicals generated from peroxides, leads to a decreased resistance of HCV infected cells in comparison to uninfected cells against toxicity of radicals. Thus, generating artificial oxidative stress conditions allows selective killing of HCV-infected cells.

Examples for useful radical forming compounds (radical initiators) are bipyridyls such as paraquat, 2,2'-bipyridyl and 4,4'-bipyridyl derivatives, bis-6-(2,2'-bipyridyl)-pyrimidines, tris-(2,2'-bipyridyl)-ruthenium, peroxides such as dibenzoylperoxide, diacetylperoxide, hydrogen peroxide, di-tert-butylperoxide, or diaza compounds such as diazaisobutyronitril.

Another aspect of the present invention is directed to a novel therapeutic composition useful for the prophylaxis and/or treatment of an individual afflicted with Hepatitis C virus and/or associated diseases comprising at least one agent capable of inactivating or inhibiting the activity of GI-GPx or of decreasing or inhibiting the production and/or expression of GI-GPx.

Yet another aspect of the present invention is directed to a novel therapeutic composition useful for the prophylaxis and/or treatment of an individual afflicted with Hepatitis C virus and/or associated diseases comprising at least one of the specific chemical substances and compounds, alone or in combination, selected from the group consisting of selenium, selenium salts, Vitamin $D_3$, and retinoids. Particularly preferred retinoids include all forms of retinoic acid, including, but not limited to, 9-cis retinoic acid, salts of 9-cis retinoic acid, $C_1$-$C_{10}$ alkyl esters of 9-cis retinoic acid, salts of $C_1$-$C_{10}$ alkyl esters of 9-cis retinoic acid, $C_1$-$C_{10}$ alkyl amides of 9-cis retinoic acid, salts of $C_1$-$C_{10}$ alkyl amides of 9-cis retinoic acid, 13-cis retinoic acid, salts of 13-cis retinoic acid, $C_1$-$C_{10}$ alkyl esters of 13-cis retinoic acid, salts of $C_1$-$C_{10}$ alkyl esters of 13-cis retinoic acid, $C_1$-$C_{10}$ alkyl amides of 13-cis retinoic acid, salts of $C_1$-$C_{10}$ alkyl amides of 13-cis retinoic acid, retinol, retinoic acid adlehyde, etretinate, N-(4-hydroxyphenyl) retinamide (4-HPR), 6-[3-(1-adamantyl)-4-hydroxyphenyl]-2-naphthalene carboxylic acid (CD437; AHPN), all-trans-retinoic acid, $C_1$-$C_{10}$ esters and amides of all-trans-retinoic acid, paraquat, 4-[E-2-(5,6,7,8-tetrahydro-5,5,8,8-tetramethyl-2-naphthalenyl)-1-propenyl]benzoic acid, 4-hydroxyphenylretinamide, and 4-[(5,6,7,8-tetrahydro-5,5,8,8-tetramethyl-2-naphthalenyl) carboxamido]benzoic acid.

A preferred selenium salt is sodium selenite. Moreover, according to a further preferred aspect of the present invention, the composition may contain a certain amount of all-trans-retinoic acid.

Further embodiments of the present invention are represented by methods for regulating the production of Hepatitis C virus in an individual or in cells, cell cultures, or cell lysates comprising the step of administering to an individual or the cells, a pharmaceutically effective amount of an agent wherein said agent activates or increases at least partially the activity of said human cellular protein gastrointestinal glutathione peroxidase or wherein said agent at least partially activates or stimulates the production of said human cellular protein gastrointestinal glutathione peroxidase.

Agents useful for this method include, but are not limited to, specific chemical substances and compounds, alone or in combination, selected from the group consisting of selenium, selenium salts, Vitamin $D_3$, and retinoids. Particularly preferred retinoids include all forms of retinoic acid, including, but not limited to, 9-cis retinoic acid, salts of 9-cis retinoic acid, $C_1$-$C_{10}$ alkyl esters of 9-cis retinoic acid, salts of $C_1$-$C_{10}$ alkyl esters of 9-cis retinoic acid, $C_1$-$C_{10}$ alkyl amides of 9-cis retinoic acid, salts of $C_1$-$C_{10}$ alkyl amides of 9-cis retinoic acid, 13-cis retinoic acid, salts of 13-cis retinoic acid, $C_1$-$C_{10}$ alkyl esters of 13-cis retinoic acid, salts of $C_1$-$C_{10}$ alkyl esters of 13-cis retinoic acid, $C_1$-$C_{10}$ alkyl amides of 13-cis retinoic acid, salts of $C_1$-$C_{10}$ alkyl amides of 13-cis retinoic acid, retinol, retinoic acid adlehyde, etretinate, N-(4-hydroxyphenyl) retinamide (4-HPR), 6-[3-(1-adamantyl)-4-hydroxyphenyl]-2-naphthalene carboxylic acid (CD437; AHPN), all-trans-retinoic acid, $C_1$-$C_{10}$ esters and amides of all-trans-retinoic acid, paraquat, 4-[E-2-(5,6,7,8-tetrahydro-5,5,8,8-tetramethyl-2-naphthalenyl)-1-propenyl]benzoic acid, 4-hydroxyphenylretinamide, and 4-[(5,6,7,8-tetrahydro-5,5,8,8-tetramethyl-2-naphthalenyl) carboxamido]benzoic acid, wherein said substances or compounds activate or increase at least partially the activity of said human cellular protein gastrointestinal glutathione peroxidase or wherein said substances or compounds at least partially activate or stimulate the production of said human cellular protein gastrointestinal glutathione peroxidase.

Further aspects of the present invention relate to methods either for regulating the expression of the human cellular protein gastrointestinal glutathione peroxidase in an individual or in cells, cell culture, or cell lysates comprising the step of administering to either to the individual or the cells, cell culture or cell lysates, a pharmaceutically effective amount of an agent wherein said agent stimulates or increases at least partially the transcription of DNA and/or the translation of RNA encoding GI-GPx.

According to the above-mentioned method another aspect of the present invention is directed to novel therapeutic compositions useful within said methods for prophylaxis and/or treatment of an individual afflicted with Hepatitis C virus and/or associated diseases. Said compositions comprise at least one agent capable of increasing the activity of GI-GPx or of activating or stimulating the production and/or expression of GI-GPx.

Agents useful in said compositions include, but are not limited to at least one of the specific chemical substances and compounds, alone or in combination, selected from the group consisting of selenium, selenium salts, Vitamin $D_3$, and retinoids. Particularly preferred retinoids include all forms of retinoic acid, including, but not limited to, 9-cis retinoic acid, salts of 9-cis retinoic acid, $C_1$-$C_{10}$ alkyl esters of 9-cis retinoic acid, salts of $C_1$-$C_{10}$ alkyl esters of 9-cis retinoic acid, $C_1$-$C_{10}$ alkyl amides of 9-cis retinoic acid, salts of $C_1$-$C_{10}$ alkyl amides of 9-cis retinoic acid, 13-cis retinoic acid, salts of 13-cis retinoic acid, $C_1$-$C_{10}$ alkyl esters of 13-cis retinoic acid, salts of $C_1$-$C_{10}$ alkyl esters of 13-cis retinoic acid, $C_1$-$C_{10}$ alkyl amides of 13-cis retinoic acid, salts of $C_1$-$C_{10}$ alkyl amides of 13-cis retinoic acid, retinol, retinoic acid adlehyde, etretinate, N-(4-hydroxyphenyl) retinamide (4HPR), 6-[3-(1-adamantyl)-4-hydroxyphenyl]-2-naphthalene carboxylic acid (CD437; AHPN), all-trans-retinoic acid, $C_1$-$C_{10}$ esters and amides of all-trans-retinoic acid, paraquat, 4-[E-2-(5,6,7,8-tetrahydro-5,5,8,8-tetramethyl-2-naphthalenyl)-1-propenyl]benzoic acid, 4-hydroxyphenylretinamide, and 4-[(5,6,7,8-tetrahydro-5,5,8,8-tetramethyl-2-naphthalenyl)carboxamido]benzoic acid, wherein said substances and compounds are capable of increasing the activity of GI-GPx or of activating or stimulating the production and/or expression of GI-GPx.

Said pharmaceutical compositions may further comprise pharmaceutically acceptable carriers, excipients, and/or diluents.

Further aspects of the present invention relate to methods either for regulating the expression of the human cellular protein gastrointestinal glutathione peroxidase in an individual or in cells, cell cultures, or cell lysates comprising the step of administering to either the individual or the cells, cell cultures, or cell lysates a pharmaceutically effective amount of an agent wherein said agent inhibits or decreases at least partially the transcription of DNA and/or the translation of RNA encoding said human cellular protein gastrointestinal glutathione peroxidase.

Therapeutics, pharmaceutically active agents or inhibitors, respectively, may be administered to cells from an individual in vitro, or may involve in vivo administration to the individual. The term "individual" preferably refers to mammals and most preferably to humans. Routes of administration of pharmaceutical preparations to an individual may include oral and parenteral, including dermal, intradermal, intragastral, intracutan, intravasal, intravenous, intramuscular, intraperitoneal, intranasal, intravaginal, intrabuccal, percutaneous, rectal, subcutaneous, sublingual, topical or transdermal application, but are not limited to these ways of administration. For instance, preferred preparations according to the invention will be in a form which is suitable for oral administration. These orally administratable forms, for example, include pills, tablets, film tablets, coated tablets, capsules, powders and deposits. Administration to an individual may be in a single dose or in repeated administrations, and may be in any of a variety of physiologically acceptable salt forms, and/or with an acceptable pharmaceutical carrier, binder, lubricant, excipient, diluent and/or adjuvant. Pharmaceutically acceptable salt forms and standard pharmaceutical formulation techniques are well known to persons skilled in the art.

As used herein, a "pharmaceutical effective amount" of a GI-GPx activator or GI-GPx inhibitor is an amount effective to achieve the desired physiological result, either in cells, cell cultures, or cell lysates treated in vitro or in a mammalian subject such as a human patient treated in vivo. Specifically, a pharmaceutically effective amount is an amount sufficient to inhibit, for some period of time, one or more of the clinically defined pathological processes associated with the viral infection. The effective amount may vary depending on the specific GI-GPx inhibitor or activator selected, and is also dependent on a variety of factors and conditions related to the subject to be treated and the severity of the infection. For example, if the inhibitor or activator is to be administered in vivo, factors such as the age, weight and health of the patient as well as dose response curves and toxicity data obtained in pre-clinical animal work would be among those considered. If the inhibitor or activator is to be contacted with the cells, cell cultures, or cell lysates in vitro, one would also design a variety of pre-clinical in vitro studies to assess such parameters as uptake, half-life, dose, toxicity, etc. The determination of a pharmaceutically effective amount for a given agent is well within the ability of those skilled in the art.

By way of illustration, a contemplated therapy according to the invention would entail administration of 1-100 mg/m$^2$/day of an oral retinoid such as all-trans-retinoic acid, preferably 20-50 mg/m$^2$/day, preferably administered in 1-4 doses/day (more preferably 1-3 doses daily, most preferably 2 doses daily). Advantageously, this retinoid administration is combined with interferon therapy, e.g., pegylated alpha interferon administered, e.g., 135-180 μg per week by subcutaneous injection. In a preferred aspect of this invention, a selenium compound such as a selenium salt may be added to this combination therapy (e.g., one 30-50 μg capsule daily).

It is also apparent to a person skilled in the art that detection includes any method known in the art useful to indicate the presence, absence, or amount of a detection target. Such methods may include, but are not limited to, any molecular or cellular techniques, used singularly or in combination, including, but not limited to: hybridization and/or binding techniques, including blotting techniques and immunoassays; labeling techniques (chemiluminescent, calorimetric, fluorescent, radioisotopic); spectroscopic techniques; separations technology, including precipitations, electrophoresis, chromatography, centrifugation, ultrafiltration, cell sorting; and enzymatic manipulations (e.g. digestion).

The present disclosure also teaches for the first time the downregulation of GI-GPx specifically involved in the viral infection of Hepatitis C virus. Thus, the present invention is also directed to a method useful for detecting novel compounds useful for prophylaxis and/or treatment of HCV infections.

The present disclosure teaches for the first time the upregulation of GI-GPx specifically involved in the viral infection of Hepatitis C virus using specific chemical compounds and substances, or combinations thereof, selected from the group consisting of selenium, selenium salts, Vitamin $D_3$, and retinoids. Particularly preferred retinoids include all forms of retinoic acid, including, but not limited to, 9-cis retinoic acid, salts of 9-cis retinoic acid, $C_1$-$C_{10}$ alkyl esters of 9-cis retinoic acid, salts of $C_1$-$C_{10}$ alkyl esters of 9-cis retinoic acid, $C_1$-$C_{10}$ alkyl amides of 9-cis retinoic acid, salts of $C_1$-$C_{10}$ alkyl amides of 9-cis retinoic acid, 13-cis retinoic acid, salts of 13-cis retinoic acid, $C_1$-$C_{10}$ alkyl esters of 13-cis retinoic acid, salts of $C_1$-$C_{10}$ alkyl esters of 13-cis retinoic acid, $C_1$-$C_{10}$ alkyl amides of 13-cis retinoic acid, salts of $C_1$-$C_{10}$ alkyl amides of 13-cis retinoic acid, retinol, retinoic acid adlehyde, etretinate, N-(4-hydroxyphenyl) retinamide (4-HPR), 6-[3-(1-adamantyl)-4-hydroxyphenyl]-2-naphthalene carboxylic acid (CD437; AHPN), all-trans-retinoic acid, $C_1$-$C_{10}$ esters and amides of all-trans-retinoic acid, paraquat, 4-[E-2-(5,6,7,8-tetrahydro-5,5,8,8-tetramethyl-2-naphthalenyl)-1-propenyl]benzoic acid, 4-hydroxyphenylretinamide, and 4-[(5,6,7,8-tetrahydro-5,5,8,8-tetramethyl-2-naphthalenyl)carboxamido]benzoic acid.

The present invention provides methods to identify compounds useful for prophylaxis and/or treatment of HCV infections by screening a test compound, or a library of test compounds, for its ability to inhibit or activate GI-GPx, identified herein as characteristically downregulated during HCV growth and RNA replication inside a cell or individual. A variety of assay protocols and detection techniques are well known in the art and easily adapted for this purpose by a skilled practitioner. Such methods include, but are not limited to, high throughput assays (e.g., microarray technology, phage display technology), and in vitro and in vivo cellular and tissue assays.

In a related aspect, the present invention provides, in view of the important role of GI-GPx in the HCV infection and/or replication process, an assay component especially useful for detecting HCV in an individual, in cells, cell cultures, or cell lysates. Preferably the assay component comprises oligonucleotides immobilized on a solid support capable of detecting GI-GPx activity. Preferably the solid support would contain oligonucleotides of sufficient quality and quantity to detect all of the above-mentioned human cellular proteins (e.g., a nucleic acid microarray).

Similarly, it is an object of the present invention to provide an assay component especially useful for screening compounds for the prophylaxis and/or treatment of HCV infections. One preferred assay component comprises oligonucleotides that encode GI-GPx immobilized on a solid support.

The polypeptide product of gene expression may be assayed to determine the amount of expression as well. Methods for assaying for a protein include, but are not limited to, Western Blotting, immuno-precipitation, radio-immuno-assay, immuno-histochemistry and peptide immobilization in an ordered array. It is understood, however, that any method for specifically and quantitatively measuring a specific protein or mRNA product can be used.

The present invention further incorporates by reference in their entirety techniques well known in the field of microarray construction and analysis. These techniques include, but are not limited to, techniques described in the following patents and patent applications describing array of biopolymeric compounds and methods for their fabrication:

U.S. Pat. Nos. 5,242,974; 5,384,261; 5,405,783; 5,412,087; 5,424,186; 5,429,807; 5,436,327; 5,445,934; 5,472,672; 5,527,681; 5,529,756; 5,545,531; 5,554,501; 5,556,752; 5,561,071; 5,559,895; 5,624,711; 5,639,603; 5,658,734; 5,807,522; and 6,087,102; international patent publications WO 93/17126; WO 95/11995; and WO 95/35505; European patent publications EP 742 287 and EP 799 897.

Suitable techniques also include, but are not limited to, techniques described in the following patents and patent application describing methods of using arrays in various applications:

U.S. Pat. Nos. 5,143,854; 5,288,644; 5,324,633; 5,432,049; 5,470,710; 5,492,806; 5,503,980; 5,510,270; 5,525,464; 5,547,839; 5,580,732; 5,661,028; 5,994,076; 6,033,860; 6,040,138; 6,040,140; international patent publications WO 95/21265; WO 96/31622; WO 97/10365; and WO 97/27317; European patent publications EP 373 203 and EP 785 280.

It will be readily apparent to those skilled in the art that other suitable modifications and adaptations of the compositions and methods of the invention described herein are evident and may be made and used without departing from the scope of the invention or the embodiments disclosed herein. Having now described the present invention in detail, the same will be more clearly understood by reference to the following examples, which are included for purposes of illustration only and are not intended to be limiting of the invention.

EXAMPLES

1. Human cDNA-Arrays on Membranes

Atlas™ Human Stress Array (Catalog #: 7747-1) from Clontech (Clontech Laboratories, Palo Alto, Calif. 94303, USA) were used. This array includes 234 human cDNAs immobilized in duplicate dots (10 ng of cDNA per dot) on a nylon membrane.

2. Cellular HCV RNA Replication System

HuH-pcDNA3, HuH-9-13, HuH-5-15 and HuH-11-7 cells were grown in DMEM (Dulbecco's Modified Eagle's Medium) supplemented with 10% FCS (fetal calf serum), 2 mM Glutamine, Penicillin (100 IU/ml) /Streptomycin (100 µg/ml) and 1× nonessential amino acids in the presence of 1 mg/ml G-418. Cells were routinely passaged three times a week at a dilution of 1:3 or 1:2.

3. Lysis of Cells, and Isolation of Total RNA

HuH-pcDNA3, HuH-9-13, HuH-5-15 and HuH-11-7 cells were seeded at $5 \times 10^5$ cells per 10 cm plate in medium without G-148. The medium was changed 3 days after plating and cells were harvested 5 days after plating by lysing the cells directly on the plate with 4 ml of Tri-reagent (Molecular Research Center, Inc., USA). The lysates were stored at room temperature for 5 minutes and then centrifuged at 12000×g for 15 minutes at 4° C. The supernatant was mixed with 0.1 ml of 1-bromo-3-chloropropane per 1 ml of Tri-reagent and vigorously shaken. The suspension was stored for 5 minutes at room temperature and then centrifuged at 12000×g for 15 minutes at 4° C. The colorless upper phase was transferred into new tubes, mixed with 5 µl of polyacryl-carrier (Molecular Research Center Inc., USA) and with 0.5 ml of isopropanol per 1 ml of Tri-reagent and vigorously shaken. The samples were stored at room temperature for 5 minutes and then centrifuged at 12000×g for 8 minutes at 4° C. The supernatant was removed and the RNA pellet washed twice with 1 ml of 75% ethanol. The pellet was dried and resuspended in 25 µl of RNase-free buffer per initial 1 ml lysate.

4. Preparation of Radioactively Labeled cDNA Probes from RNA

In order to obtain radioactively labeled cDNA probe, RNA was transcribed into a cDNA-probe in the presence of radioactively labeled dATP. Six µg of total RNA was labeled with 100 µCi [$^{33}$P]-dATP (Amersham, UK) according to the protocol provided by Clontech. Subsequently, the reaction was stopped by adding 5 µl 0.5M EDTA (ethylene diamine tetraacetate) and 25 µl 0.6M NaOH and incubation for 30 minutes at 68° C.

Unincorporated nucleotides were removed from the labeling reaction using ProbeQuant G-50 columns (Amersham, UK). The column was vigorously shaken and centrifuged for 1 minute at 735×g in an appropriate reaction tube after bottom closure and lid were removed. The column was placed into a new reaction tube, the probe was applied onto the center of a column material and the column was centrifuged for 2 minutes at 735×g. The flow-through was transferred into new reaction tubes and filled up to a volume of 100 µl with 10 mM Tris, pH 7.4, 1 mM EDTA. The probe was precipitated by centrifugation for 15 minutes at 12000×g after 4 µl of 5M NaCl, 1 µl poly-acryl-carrier (Molecular Research Centre, Inc., USA) and 250 µl ethanol were added. The supernatant was discarded and the pellet dried before starting with the hybridization.

5. Hybridization of Radioactively Labeled cDNA-Probes to cDNA-Arrays

The pellet was resuspended in 10 µl $C_0$t-1 DNA (1 µg/µl, Roche Diagnostics, Germany), 10 µl yeast tRNA (1 µg/µl Sigma, USA) and 10 µl polyA (1 µg/µl), Roche Diagnostics, Germany). Herring sperm DNA was added to a final concentration of 100 µg/ml and the volume was filled up to 100 µl with 5 µl 10% SDS (Sodiumdodecylsulfate), 25 µl 20×SSC (3 M NaCl, 300 mM Sodium Citrate, pH 7.0) and bidistilled $H_2O$. The mix was put on 95° C. for 5 minutes, centrifuged for 30 seconds at 10000×g and vigorously shaken for 60 minutes at 65° C. A 1 µl aliquot of the probe was used to measure the incorporation of radioactive dATP with a scintillation counter. Probes with at least a total of 20×10$^6$ cpm were used. The arrays were prehybridized for at least 3 hours at 65° C. in hybridization solution in a roller bottle oven. After prehybridization the radioactively labeled probe was added into the hybridization solution and hybridization was continued for 20 hours. The probe was discarded and replaced with wash solution A (2×SSC). The arrays were washed twice in wash solution A at room temperature in the roller oven. Afterwards, wash solution A was replaced by wash solution B (2×SSC, 0.5% SDS) preheated to 65° C. and arrays were washed twice for 30 minutes at 65° C. Then, wash solution B was replaced by wash solution C (0.5×SSC, 0.5% SDS) preheated to 65° C. and arrays were washed twice for 30 minutes at 65° C. The moist arrays were wrapped in airtight bags and exposed for 8 to 72 hours on erased phospho-imager screens (Fujifilm, Japan).

6. Analysis of cDNA-Arrays

The exposed phospho-imager screens were scanned with a resolution of 100 µm and 16 bits per pixel using a BAS-1800 (Fujifilm, Japan). Files were imported into the computer program ArrayVision (Imaging Research, Canada). Using the program's features, the hybridization signals of each target cDNA were converted into numbers. The strength of the hybridization signals reflected the quantity of RNA molecules present in the probe. Differentially expressed genes were selected according to the ratio of their signal strength after normalization to the overall intensity of the arrays.

7. Results

Comparing the expression pattern of signal transduction mRNAs in HCV Replicon cells HuH-9-13, HuH-5-15, and HuH-11-7 and HuH-pcDNA control cells which do not contain HCV replicons using cDNA-arrays on membranes, the human gastrointestinal glutathione peroxidase (P18283) gene was identified as anti-HCV target. The mRNA levels were down-regulated to 2.8% in HuH-9-13, to 8.3% in HuH-5-15 and to 6.1% in HuH-11-7 cells compared to non-infected HuH-pcDNA control cells.

8. Northern Blotting

Ten (10) µg total RNA of each cell line was separated in a 1.2% agarose-formaldehyde gel, transferred on nylon membrane (Amersham) and hybridized with two different oligo-desoxyribonucleotides. Their sequences were derived from the coding (5'-TGGTTGGG AAGGTGCGGCTG-TAGC GTC GGAAGGGC-3'; SEQ ID NO:1) and 3'-untranslated (5'-CCTCTCAGACACCACCCATGAGGGTT-TAGGAAGGTGCCAT-3'; SEQ ID NO:2) region of the human gastrointestinal glutathione peroxidase (P18283) gene. Labeling was performed by 3'-end tailing with $^{32}$P-dCTP and terminal transferase (Roche Diagnostics GmbH, Mannheim, Germany). Northern Blotting membranes were hybridized with the labeled oligonucleotides overnight at 65° C. and unspecifically bound probe washed away.

After final washing (1×SSC, 1% SDS at 60° C. for 30 min.), bound probe was detected by autoradiography for 12 hrs at −70° C. using an x-ray film (Fuji) and quantified with a phospho-imager.

9. Confirmation of Expression Pattern by Northern Blotting

Figure 1:
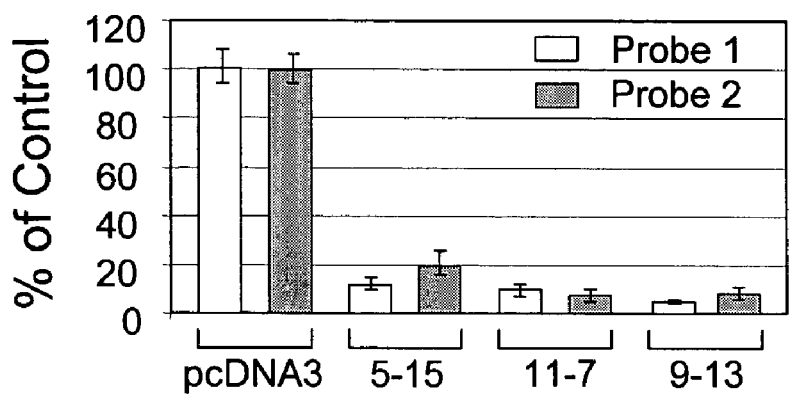
FIG. 1:
Replicon cells express less GI-GPx mRNA than control HuH7 cells:
HuH7 control cells (pcDNA3) and the HuH7 replicon cell lines 5-15, 11-7 and 9-13 were plated in 10-cm culture dishes ($5 \times 10^5$ cells/58 cm$^2$) and harvested after three days when cells were actively progressing through the cell cycle. Total RNA was isolated and 10 µg separated in a 1.2% agarose gel and used for Northern blot analysis.
Figure 1:
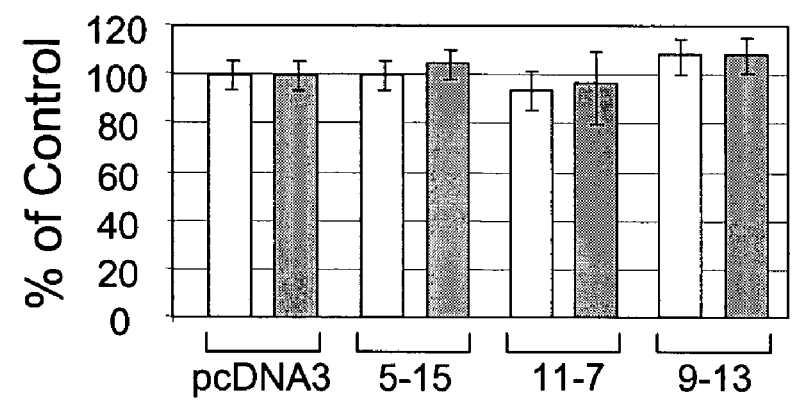

Northern blot analysis was performed with two oligonucleotide probes derived from the human gastrointestinal glutathione peroxidase cDNA. Hybridization resulted in detection of one RNA of about 1 kb in HuH-pcDNA3 cells, but no or only weak detection of this band in HCV-replicon carrying cells. Therefore, analysis of the Northern Blotting signals confirmed precisely the down-regulation previously observed in the filter array hybridization (cf. section 6., supra; FIG. 1).

10. Glutathione Peroxidase Activity is Reduced in Replicon Cell Lines

Measuring the glutathione peroxidase activity utilizing tert-butyl hydroperoxide as substrate, revealed that the replicon cells exhibited reduced glutathione peroxidase activity (see FIG. 2).

Methods:

For measuring cellular glutathione peroxidase activity, the description of the kit's manufacturer (Calbiochem) was followed. Briefly, cells were washed with ice-cold PBS (phosphate buffered saline), harvested with a rubber policeman in 5 mM EDTA, 1 mM DTT (dithiothreitol) and 50 mM Tris-HCl (Tris-(hydroxymethyl)-aminomethane-hydrochloride), pH 7.5 and lysed by three cycles of freezing and thawing. After spinning for 15 min at 10,000×g (4° C.) protein concentration of the supernatant was determined with the BCA reagents (Pierce, Bruchsal, Germany). 180 µg protein were used per assay.

Tert-butyl hydroperoxide was used as substrate and GI-GPx activity was estimated indirectly. Oxidized glutathione, produced upon reduction of the peroxide by GI-GPx, is recycled to its reduced state by glutathione reductase by oxidation of NADPH+H$^+$ to NADP$^+$. The oxidation of NADPH is accompanied by a decrease in absorbance at 340 nm ($A_{340}$), which provides a spectrophotometric means of monitoring GI-GPx activity. Thus, the rate of decrease in the $A_{340}$ (delta E in FIG. 2) is directly proportional to the GI-GPx activity in the sample.

11. Sensitivity of Replicon Cells Towards Paraquat

Treating mock transfected and replicon cells with increasing amounts of paraquat, a compound which produces radicals intracellularly, showed enhanced susceptibility of replicon cells against this drug.

Paraquat impaired the viability of replicon cells more severely than of pcDNA3 control cells (FIG. 3). The estimated $LD_{50}$ values for paraquat calculated from three independent experiments were 260±50 µM for HuH 9-13, 270±75 µM for HuH 5-15, 310±65 µM for HuH 11-7 and 1250±120 µM for HuH pcDNA3 (cf FIG. 3).

Methods:

Replicon cell lines and control cells were incubated for 24 hours with various concentrations of paraquat (methylviologen), and viability of the cultures was measured using the Alamar Blue assay.

For quantification of the degree of cell death in cell culture we employed the viability assay based on the reduction of tetrazolium salt to formazan by mitochondrial dehydrogenase activity. The assay was performed in 96-well microtiter plates (Greiner, Frickenhausen, Germany) as described previously (T. Herget et al., 1998, *J. Neurochem.*, 70: 47-58) but Alamar Blue (Roche Molecular Biochemicals, Germany) was used instead of MTT. The light absorbance at 405 nm of the medium including all factors but without cells was determined and subtracted from the absorption readings with cells. Eight wells per sample point were analyzed and each experiment was repeated independently at least three times.

12. Inverse Regulation of HCV Replication and GI-GPx Expression

Replicon cells were incubated with alpha interferon (IFN-α) for two and four days. Northern blot analyses were performed with 10 μg total RNA. The IFN-α treatment (1000 U/ml) caused a time- and dose-dependent downregulation of the HCV-replicon RNA and the HCV protein NS5a. An inverse correlated expression was observed for GI-GPx, i.e., GI-GPx was up-regulated within four days of interferon treatment. Interferon had no effect on the expression of GI-GPx in mock transfected HuH7 cells (cf FIG. 4).

13. Ectopic Expression of GI-GPx in Replicon Cell Lines

The cDNA coding for the GI-GPx was cloned by RT-PCR from HuH7 cells. Transient expression of the GI-GPx protein in HEK293 cells caused an increase of glutathione peroxidase activity demonstrating its functionality. The construct was recombined into the genome of Adenovirus. Adenovirus carrying the GI-GPx cDNA was produced and used for transduction of the GI-GPx cDNA into HuH7 and replicon cells. Western blot analyses performed 4 and 7 days after transfection showed a drastic down-regulation of the HCV protein NS5a. Such a down-regulation was not observed when 'empty' or the GFP (green fluorescent protein) gene-containing Adeno virus was used in parallel (cf. FIGS. 5 and 6).

Methods:

The adenoviruses used here were all E1, E3 defective derivatives of adenovirus type 5 (W. C. Russell, 2000, *J. Gen. Virol.*, 81: 2573-2604). The coding region for GI-GPx (0.7 kb) was amplified by PCR using an upstream primer containing an HindIII recognition site (5'-GCG CAAGCT-TATGGCTTTCATTGCCAAGTCCTTC-3', start codon underlined italics; SEQ ID NO:3) and a downstream primer containing an XbaI site (5'-GTTCATCTAGATATGGCAAC TTTAAGGAGGCGCTTG-3'; SEQ ID NO:4) but without stop-codon to allow expression of fusion proteins with HIS- and VSV-tag. The 3'-UTR (0.3 kb) of the GI-GPx mRNA, containing a SECIS (selenocysteine inserting sequence), was amplified using the up-stream primer 5'-GCC CTC-GAGATGTGAACTGCTCAACACACAG-3' (SEQ ID NO:5) with an XhoI recognition site and the down-stream primer 5'-CCACGCGGCCGCTTTATTGGTCTCT-TCTAGCAGAGT GGC-3' (SEQ ID NO: 6) covering the polyadenylation site (AAUAAA) and containing a NotI restriction site for cloning. RNA isolated from HuH7 cells were reverse transcribed and used as template for PCR. The cDNA coding for human GI-GPx was cloned into the transfer plasmid (pPM7) between the CMV (cytomegalovirus) immediately early promoter/enhancer and the rabbit beta-globin intron/polyadenylation signal. This expression cassette was inserted into a bacterial plasmid borne-adenovirus genome using recombination in bacteria (C. Chartier et al., 1996, *J. Virol.*, 70: 4805-4810). A cloned version of the novel genome was identified, the viral genome was released from the plasmid by restriction enzyme digestion and virus replication was initiated by transfecting the genome into HEK 293 cells using a modified PEI transfection method (A.-I. Michou et al., 1999, *J. Virol.*, 73: 1399-1410). Virus was amplified in modified HEK 293 cells (F. L. Graham et al., 1977, *J. Gen. Virol.*, 36: 59-74) and purified from cell lysates using CsCl density gradient centrifugation as described (M. Cotten et al., "Adenovirus polylysine DNA conjugates," in *Current Protocols in Human Genetics* (John Wiley and Sons, Inc.; New York 1996), pp. 12.3.1-12.3.33). Virus was quantified by protein content using the conversion factor 1 mg/ml pure virion protein=$3.4 \times 10^{12}$ viral particles/ml (P. Lemay et al., 1980, *Virology*, 101: 131-143). The control viruses AdJ5 and AdLuc were previously described (J. B. Glotzer et al., 2001, *J. Virol.*, 75: 2421-2434; J. B. Glotzer et al., 2000, *Nature*, 407: 207-211).

14. Testing of GI-GPx Regulators

As a model system for HCV replication there were utilized three replicon cell lines provided by Prof. R. Bartenschlager (University of Heidelberg, Germany). Cultures were treated for various periods of time with all transretinoic acid (RA) for comparative purposes and the other agents selenium, selenium salts, Vitamin $D_3$ and retinoids, like 9-cis-retinoic acid, $C_1$-$C_{10}$ alkyl esters of 9-cis-retinoic acid, $C_1$-$C_{10}$ alkyl amides of 9-cis-retinoic acid, N-(4-hydroxyphenyl) retinamide (4-HPR), 6-[3-(1-adamantyl)-4-hydroxyphenyl]-2-naphthalene carboxylic acid (CD437; AHPN) (obtained from Sigma), paraquat, 4-[E-2-(5,6,7,8-tetrahydro-5,5,8,8-tetramethyl-2-naphthalenyl)-1-propenyl] benzoic acid, 4-hydroxyphenylretinamide, and 4-[(5,6,7,8-tetrahydro-5,5,8,8-tetramethyl-2-naphtalenyl)carboxamido] benzoic acid.

Levels of GI-GPx protein expression were measured by Western Blotting using antibodies provided by Prof. Brigelius-Flohe (University of Potsdam, Germany), and RNA levels were measured by Northern blotting using GI-GPx-specific oligonucleotides as probes. Levels of HCV RNA were investigated by Northern Blotting using a DNA oligonucleotide complementary to the neomycin phosphotransferase gene as probe. Concentration of the viral protein NS5a was determined by Western Blotting with an NS5a-specific antibody (Biogenesis, UK).

GI-GPx is drastically down-regulated in HCV replicon cells compared with mock-transfected HuH7 cells. Forcing replicon cells to re-express GI-GPx (e.g. by infection with GI-GPx containing Adenovirus) results in reduction of subgenomic HCV RNA and of the HCV protein NS5a to barely detectable levels. According to the present invention the discovery of this inverse correlation was used to develop a method to up-regulate the expression of the cellular, endogenous GI-GPx gene. This up-regulation in replicon cells causes a depletion of HCV.

Treatment of replicon cells for three days with all-trans-retinoic acid (1 μM) had hardly any effect on GI-GPx and HCV expression. However, after seven days of incubation, a drastic up-regulation of GI-GPx, both at the RNA and protein level (three- to ten-fold) was observed. Concomitantly, expression of subgenomic HCV RNA and of viral protein NS5a was downregulated two- to five-fold, depending on the cell line investigated. Furthermore, it was surprisingly found that a further downregulation of HCV-RNA and NS5a protein was dependent on the addition of selenium or a selenium salt, e.g., sodium selenite (50 nM). This fact implies that downregulation of HCV was promoted firstly by activation of the GI-GPx gene on transcriptional level by retinoic acid and secondly by the synthesis of selenoprotein(s) for which sodium selenite was needed. Indeed it could be shown that all-trans-retinoic acid-induced downregulation of HCV is independent of the innate immune response induced by interferon. Thus, all-trans-retinoic acid did not induce the transcription of PKR (double strand RNA-dependent protein kinase). Severe cytotoxic effects were neither observed for all-trans-retinoic acid nor for sodium selenite, or both in combination.

The presented findings show that retinoids (in combination with selenium or selenium salts like sodium selenite and cAmp or cAmp analogues) can be used for the treatment of HCV-positive patients. Especially the use of retinoids with high specificity for induction of the GI-GPx, like N-(4-hydroxyphenyl) retinamide (4-HPR) and 6-[3-(1-adamantyl)-4-hydroxyphenyl]-2-naphthalene carboxylic acid (CD437; AHPN), are preferred. 4-HPR and AHPN display significant potential as therapeutic agents in the prophylaxis and treatment of a number of premalignant and malignant conditions in the context of HCV infections. Indeed, the obtained data show that next to all trans-retinoic acid, other nuclear receptor ligands, including 9-cis retinoic acid, salts of 9-cis retinoic acid, $C_1$-$C_{10}$ alkyl esters of 9-cis retinoic acid, salts of $C_1$-$C_{10}$ alkyl esters of 9-cis retinoic acid, $C_1$-$C_{10}$ alkyl amides of 9-cis retinoic acid, salts of $C_1$-$C_{10}$ alkyl amides of 9-cis retinoic acid, 13-cis retinoic acid, salts of 13-cis retinoic acid, $C_1$-$C_{10}$ alkyl esters of 13-cis retinoic acid, salts of $C_1$-$C_{10}$ alkyl esters of 13-cis retinoic acid, $C_1$-$C_{10}$ alkyl amides of 13-cis retinoic acid, salts of $C_1$-$C_{10}$ alkyl amides of 13-cis retinoic acid, retinol, retinoic acid adlehyde, etretinate, N-(4-hydroxyphenyl) retinamide (4-HPR), 6-[3-(1-adamantyl)-4-hydroxyphenyl]-2-naphthalene carboxylic acid (CD437; AHPN), all-trans-retinoic acid, $C_1$-$C_{10}$ esters and amides of all-trans-retinoic acid, paraquat, 4-[E-2-(5,6,7,8-tetrahydro-5,5,8,8-tetramethyl-2-naphthalenyl)-1-propenyl]benzoic acid, acid, 4-hydroxyphenylretinamide, and 4-[(5,6,7,8-tetrahydro-5,5,8,8-tetramethyl-2-naphthalenyl)carboxamido]benzoic acid, are also capable of reducing HCV load.

All-trans-retinoic acid on replicon cells for six days led to an upregulation of GI-GPx RNA and protein due to the fact that the GI-GPx promoter contains three retinoic acid receptor recognition elements. In the presence of selenium or a selenium salt like sodium selenite, a two-to five-fold reduction of HCV RNA and HCV NS5a protein was observed in the absence of toxic effects.

Moreover, also the specific retinoids, 9-cis retinoic acid, salts of 9-cis retinoic acid, $C_1$-$C_{10}$ alkyl esters of 9-cis retinoic acid, salts of $C_1$-$C_{10}$ alkyl esters of 9-cis retinoic acid, $C_1$-$C_{10}$ alkyl amides of 9-cis retinoic acid, salts of $C_1$-$C_{10}$ alkyl amides of 9-cis retinoic acid, 13-cis retinoic acid, salts of 13-cis retinoic acid, $C_1$-$C_{10}$ alkyl esters of 13-cis retinoic acid, salts of $C_1$-$C_{10}$ alkyl esters of 13-cis retinoic acid, $C_1$-$C_{10}$ alkyl amides of 13-cis retinoic acid, salts of $C_1$-$C_{10}$ alkyl amides of 13-cis retinoic acid, retinol, retinoic acid adlehyde, etretinate, N-(4-hydroxyphenyl) retinamide (4-HPR), 6-[3-(1-adamantyl)-4-hydroxyphenyl]-2-naphthalene carboxylic acid (CD437; AHPN), all-trans-retinoic acid, $C_1$-$C_{10}$ esters and amides of all-trans-retinoic acid, paraquat, 4-[E-2-(5,6,7,8-tetrahydro-5,5,8,8-tetramethyl-2-naphthalenyl)-1-propenyl]benzoic acid, 4-hydroxyphenylretinamide, and 4-[(5,6,7,8-tetrahydro-5,5,8,8-tetramethyl-2-naphthalenyl)carboxamido]benzoic acid, alone or in combination with each other or with selenium or a selenium salt showed a similar effect.

15. Clinical Study

A randomised, single blinded clinical study was designed, to test the safety, tolerability and preliminary efficacy of all-trans-retinoic acid alone or in combination with pegylated alpha interferon in patients with chronic Hepatitis C infection. In particular, patients who failed to respond to and/or relapsed from previous interferon and ribavirin therapy will be targeted to further prove the efficacy of the suggested treatment for patients who do not respond to interferon.

The clinical study anticipates a total of 20 patients randomly selected from a pool of patients who failed to respond to interferon and/or interferon and ribavirin combination therapy. The patients will be separated into two groups, Group A and Group B. The following materials were selected for administration in this study:

1. Vesanoid™, 10 mg capsule (an orally administered all-trans-retinoic acid compound available from Hoffman-La Roche Ltd.);

2. Pegasys™ 180 μg (an injectable form of slow-release pegylated alpha interferon IIa available from Hoffman-La Roche Ltd.); and 3. Selen 30 ALLACT, 30 μg capsule ((an over-the-counter supplement including selenium and ALLACT, a garlic powder (Allium Sativum pulvis) and Lactobacillus Bulgaricus supplement)).

The proposed therapy regimen for Group A includes: 45 mg/m$^2$ daily Vesanoid™ in two oral doses plus Selen 30 ALLACT, 1 capsule/day p.o. 12 weeks; follow-up period 12 weeks (without treatment).

The proposed therapy regimen for Group B includes: 45 mg/m$^2$ daily Vesanoid™ in two oral doses plus Selen 30 ALLACT, 1 capsule/day p.o. plus Pegasys™ 180 μg/week subcutaneously for 12 weeks; follow-up period 12 weeks (without treatment).

The publications cited herein are incorporated by reference in their entirety.

Other variations and embodiments of the invention described herein will now be apparent to those skilled in the art without departing from the scope of the invention as defined in the claims that follow.

What is claimed is:

1. A method for inhibiting or downregulating Hepatitis C viral replication in an individual comprising the step of administering to an individual a pharmaceutically effective amount of an agent wherein said agent activates the activity of said human cellular protein gastrointestinal glutathione peroxidase or wherein said agent activates or stimulates the production of said human cellular protein gastrointestinal glutathione peroxidase, and wherein said agent is a combination of (i) selenium, or a selenium salt, and (ii) a retinoid selected from the group of: 9-cis retinoic acid, salts of 9-cis retinoic acid, C1-C10 alkyl esters of 9-cis retinoic acid, salts of C1-C10 alkyl esters of 9-cis retinoic acid, C1-C10 alkyl amides of 9-cis retinoic acid, salts of C1-C10 alkyl amides of 9-cis retinoic acid, 13-cis retinoic acid, salts of 13-cis retinoic acid, C1-C10 alkyl esters of 13-cis retinoic acid, salts of C1-C10 alkyl esters of 13-cis retinoic acid, C1-C10 alkyl amides of 13-cis retinoic acid, salts of C1-C10 alkyl amides of 13-cis retinoic acid, retinol, retinoic acid aldehyde, etretinate, N-(4-hydroxyphenyl) retinamide (4-HPR), 6-[3-(1-adamantyl)-4-hydroxyphenyl]-2-naphthalene carboxylic acid (CD437; AHPN), all-trans-retinoic acid, C1-C10 esters and amides of all-trans-retinoic acid, paraquat, 4-[E-2-(5,6,7,8-tetrahydro-5,5,8,8-tetramethyl-2-naphthalenyl)-1-propenyl]benzoic acid, 4-hydroxyphenyl-retinamide, and 4-[(5,6,7,8-tetrahydro-5,5,8,8-tetramethyl-2-naphthalenyl)carboxamido]benzoic acid.

2. A method for inhibiting or downregulating Hepatitis C viral replication in cells, cell culture, or cell lysates comprising the step of administering a pharmaceutically effective amount of an agent wherein said agent activates the activity of said human cellular protein gastrointestinal glutathione peroxidase or wherein said agent activates or stimulates the production of said human cellular protein gastrointestinal glutathione peroxidase in the cells or cell culture, and wherein said agent is a combination of (i) selenium, or a selenium salt, and (ii) a retinoid selected from the group of: 9-cis retinoic acid, salts of 9-cis retinoic acid, C1-C10 alkyl esters of 9-cis retinoic acid, salts of C1-C10 alkyl esters of 9-cis retinoic acid, C1-C10 alkyl amides of 9-cis retinoic acid, salts of C1-C10 alkyl amides of 9-cis retinoic acid, 13-cis retinoic acid, salts of 13-cis retinoic acid, C1-C10 alkyl esters of 13-cis retinoic acid, salts of C1-C10 alkyl esters of 13-cis retinoic acid, C1-C10 alkyl amides of 13-cis retinoic acid, salts of C1-C10 alkyl amides of 13-cis retinoic acid, retinol, retinoic acid adlehyde, etretinate, N-(4-hydroxyphenyl) retinamide (4-HPR), 6-[3-(1-adamantyl)-4-hydroxyphenyl]-2-naphthalene carboxylic acid (CD437; AHPN), all-trans-retinoic acid, C1-C10 esters and amides of all-trans-retinoic acid, paraquat, 4-[E-2-(5,6,7,8-tetrahydro-5,5,8,8-tetramethyl-2-naphthalenyl)-1-propenyl]benzoic acid, 4-hydroxyphenylretinamide, and 4-[(5,6,7,8-tetrahydro-5,5,8,8-tetramethyl-2-naphthalenyl) carboxamido]benzoic acid.

3. The method according to claim 1, wherein said individual fails to respond to interferon therapy.

4. The method according to any one of claims 1, 2, or 3, wherein said combination includes (i) a selenium salt and (ii) all-trans-retinoic acid, 9-cis retinoic acid, or 13-cis retinoic acid.

5. The method according to any one of claims or 1, 2, or 3, wherein said combination further includes alpha interferon or pegylated alpha interferon.

6. The method according to any one of claims 1, 2, or 3, wherein said combination further includes ribavirin.

7. The method according to claim 4, wherein said combination further includes alpha interferon or pegylated interferon.

8. The method according to claim 4, wherein said combination further includes ribavirin.

9. The method according to claim 5, wherein said combination further includes ribavirin.

10. The method according to claim 7, wherein said combination further includes ribavirin.

* * * * *

SEQUENCE LISTING

<160> NUMBER OF SEQ ID NOS: 6

<210> SEQ ID NO 1
<211> LENGTH: 35
<212> TYPE: DNA
<213> ORGANISM: Homo sapiens

```
<400> SEQUENCE: 1
tggttgggaa ggtgcggctg tagcgtcgga agggc                                35

<210> SEQ ID NO 2
<211> LENGTH: 40
<212> TYPE: DNA
<213> ORGANISM: Homo sapiens

<400> SEQUENCE: 2
cctctcagac accaccatg agggtttagg aaggtgccat                            40

<210> SEQ ID NO 3
<211> LENGTH: 34
<212> TYPE: DNA
<213> ORGANISM: Homo sapiens

<400> SEQUENCE: 3
gcgcaagctt atggctttca ttgccaagtc cttc                                 34

<210> SEQ ID NO 4
<211> LENGTH: 36
<212> TYPE: DNA
<213> ORGANISM: Homo sapiens

<400> SEQUENCE: 4
gttcatctag atatggcaac tttaaggagg cgcttg                               36

<210> SEQ ID NO 5
<211> LENGTH: 31
<212> TYPE: DNA
<213> ORGANISM: Homo sapiens

<400> SEQUENCE: 5
gccctcgaga tgtgaactgc tcaacacaca g                                    31

<210> SEQ ID NO 6
<211> LENGTH: 39
<212> TYPE: DNA
<213> ORGANISM: Homo sapiens

<400> SEQUENCE: 6
ccacgcggcc gctttattgg tctcttctag cagagtggc                            39
```